(12) United States Patent
Iggo et al.

(10) Patent No.: US 6,544,507 B2
(45) Date of Patent: Apr. 8, 2003

(54) ANTI-NEOPLASTIC VIRAL AGENTS

(75) Inventors: Richard Iggo, Lausanne (CH); Michele Alberto Brunori, Lyons (FR)

(73) Assignee: BTG International Limited, London (GB)

(*) Notice: Subject to any disclaimer, the term of this patent is extended or adjusted under 35 U.S.C. 154(b) by 0 days.

(21) Appl. No.: 09/916,510

(22) Filed: Jul. 30, 2001

(65) Prior Publication Data

US 2002/0168349 A1 Nov. 14, 2002

Related U.S. Application Data

(63) Continuation of application No. PCT/GB00/01142, filed on Mar. 24, 2000.

(30) Foreign Application Priority Data

Mar. 24, 1999 (GB) .............................................. 9906815

(51) Int. Cl.⁷ ........................ A61K 48/00; A61K 35/76; C12N 7/01; C12N 15/861
(52) U.S. Cl. ................ 424/93.2; 435/320.1; 435/235.1; 435/471; 435/475; 435/91.4; 435/91.33; 514/44
(58) Field of Search ............................... 435/235.1, 236, 435/320.1, 474–477, 483, 488, 471, 91.4, 91.33; 536/23.72; 424/93.2; 514/44

(56) References Cited

U.S. PATENT DOCUMENTS 5,998,205 A * 12/1999 Hallenbeck et al. ........ 435/325

FOREIGN PATENT DOCUMENTS

| WO | 94/18992 | 2/1994 | |
| WO | 96/34969 | 5/1996 | |
| WO | 96/17053 | 6/1996 | |
| WO | 96/36365 | 11/1996 | |
| WO | 98/13508 | 9/1997 | |
| WO | 98/35028 | 1/1998 | |
| WO | 98/39464 | 3/1998 | |
| WO | 98/41631 | 3/1998 | |
| WO | 98/39464 | * 9/1998 | ........... C12N/15/86 |
| WO | 99/25860 | 5/1999 | |

OTHER PUBLICATIONS

Korinek et al Science 275(Mar. 21, 1997): 1784–1787.*
Ketner et al PNAS USA 91:6186–6190, 1994.*
Monaco et al TIBTECH 12:280–286, 1994.*

"Sequence of the immunoregulatory early region 3 and flanking sequences of adenovirus type 35", Christopher F Basler et al, Gene. 170 (1996) P 249–254.

"Adenovirus early region 3 promoter regulation by E1A/£1B is independent of alterations in DNA binding and gene activation of CREB/ATF and AP1", Masayo Kornuc et al, Journal of Virology, May 1990, P 2004–2013.

"Activation of the transcription factor Gli1 and the sonic hedgehog signalling pathway in skin tumours", N Dahmane et al, Nature, vol. 389, No. 389, Oct. 23, 1997, P876–881.

"Expression of the RAG–2 gene in murine central nervous system tumor cell lines", Tomokazu Aoki et al, Biochemical and Biophysical Research Communications, vol. 181, No. 1, Nov. 27, 1991, P151–158.

"Targeting gene expression to hypoxic tumor cells", Gabi U Dachs et al, Nature Medicine, vol. 3, No. 5, May 1997, P 515–520.

"The human telomerase catalytic subunit hTERT: organization of the gene and characterization of the promoter", Yu–Sheng Cong et al, Human Molecular Genetics, vol. 8, No. 1, 1999, P 137–142.

"Mutational Analysis of the APC/β–Catenin/Tcf pathway in colorectal cancer", Andrew B Sparks et al, Cancer Research 58, Mar. 15, 1998, P 1130–1134.

"Generation of fiber–mutant recombinant adenoviruses for gene therapy of malignant glioma", Yoko Yoshida et al, Human Gene Therapy 9, Nov. 20, 1998, P 2503–2515.

* cited by examiner

Primary Examiner—Mary E. Mosher
(74) Attorney, Agent, or Firm—Nixon & Vanderhye

(57) ABSTRACT

A viral DNA construct, and virus encoded thereby, is provided having one or more tumor specific transcription factor binding sites in place of one or more wild type transcription factor binding sites operatively positioned in the promoter region which controls expression of early genes responsible for viral nucleic acid replication. Preferred constructs place the tumor specific transcription factor binding sites in operative relation to DNA polymerase, DNA terminal protein and/or DNA binding protein. Compositions and constructs contained therein are provided, particularly for use in therapy. Methods of treating patients for neoplasms are also provided.

23 Claims, 19 Drawing Sheets

Fig.1.

```
      ...33k protein →
1   GGA GCG CTG CGT CTG GCG CCC AAC GAA CCC GTA TCG ACC CGC GAG CTT AGA AAC AGG ATT
    G   A   L   R   L   A   P   N   E   P   V   S   T   R   E   L   R   N   R   I 61  TTT CCC ACT CTG TAT GCT ATA TTT CAA CAG AGC AGG GGC CAA GAA CAA GAG CTG AAA ATA
    F   P   T   L   Y   A   I   F   Q   Q   S   R   G   Q   E   Q   E   L   K   I 121 AAA AAC AGG TCT CTG CGA TCC CTC ACC CGC AGC TGC CTG TAT CAC AAA AGC GAA GAT CAG
    K   N   R   S   L   R   S   L   T   R   S   C   L   Y   H   K   S   E   D   Q ←E2 transcription start site]                        E2 TATA box
181 CTT CGG CGC ACG CTG GAA GAC GCG GAG GCT CTC TTC AGT AAA TAC TGC GCG CTG ACT CTT
    L   R   R   T   L   E   D   A   E   A   L   F   S   K   Y   C   A   L   T   L 241 AAG GAC TAG  ...    ...   E2 promoter replacement sequence  ..   ..
    K   D   * pVIII protein →
                                          ..  GCC ATT ATG AGC AAG GAA ATT CCC ACG CCC
                                                      M   S   K   E   I   P   T   P 361 TAC ATG TGG AGT TAC CAG CCA CAA ATG GGA CTT GCG GCT GGA GCT GCC CAA GAC TAC TCA
    Y   M   W   S   Y   Q   P   Q   M   G   L   A   A   G   A   A   Q   D   Y   S
```

Fig.1 (Cont).

```
421
ACC CGA ATA AAC TAC ATG AGC GCG GGA CCC CAC ATG ATA TCC CGG GTC AAC GGA ATC CGC
 T   R   I   N   Y   M   S   A   G   P   H   M   I   S   R   V   N   G   I   R

481
GCC CAC CGA AAC CGA ATT CTC TTG GAA CAG GCG GCT ATT ACC ACC ACA CCT CGT AAT AAC
 A   H   R   N   R   I   L   L   E   Q   A   A   I   T   T   T   P   R   N   N
                    NF1                                              NFkB
541
CTT AAT CCC CGT AGT TGG CCC GCT GCC CTG GTG TAC CAG GAA AGT CCC GCT CCC ACC ACT
 L   N   P   R   S   W   P   A   A   L   V   Y   Q   E   S   P   A   P   T   T
              H4                                        L2
         NFkB                                   AP1
601 ─────────                              ────────────
GTG GTA CTT CCC AGA GAC GCC CAG GCC GAA GTT CAG ATG ACT AAC TCA GGG GCG CAG CTT
 V   V   L   P   R   D   A   Q   A   E   V   Q   M   T   N   S   G   A   Q   L
     L1                                          H3
                 ATF                                      E3 TATA box
661      ─────────                                       ──────────────
GCG GGC GGC TTT CGT CAC AGG GTG CGG TCG CCC GGG CAG GGT ATA ACT CAC CTG ACA ATC
 A   G   G   F   R   H   R   V   R   S   P   G   Q   G   I   T   H   L   T   I
              H2
                      ⌈E3 transcription start site→
721
AGA GGG CGA GGT ATT CAG CTC AAC GAC GAG TCG GTG AGC TCC TCG CTT GGT CTC CGT CCG
 R   G   R   G   I   Q   L   N   D   E   S   V   S   S   S   L   G   L   R   P
```

Fig.2.

```
        ...33k protein →
1   GGA GCG CTG CGT CTG GCG CCC AAC GAA CCC GTA TCG ACC CGC GAG CTT AGA AAC AGG ATT
    G   A   L   R   L   A   P   N   E   P   V   S   T   R   E   L   R   N   R   I 61  TTT CCC ACT CTG TAT GCT ATA TTT CAA CAG AGC AGG GGC CAA GAA CAA GAG CTG AAA ATA
    F   P   T   L   Y   A   I   F   Q   Q   S   R   G   Q   E   Q   E   L   K   I 121 AAA AAC AGG TCT CTG CGA TCC CTC ACC CGC AGC TGC CTG TAT CAC AAA AGC GAA GAT CAG
    K   N   R   S   L   R   S   L   T   R   S   C   L   Y   H   K   S   E   D   Q
                                        ←E2 transcription start site]           E2 TATA box
181 CTT CGG CGC ACG CTG GAA GAC GCG GAG GCT CTC TTC AGT AAA TAC TGC GCG CTG ACT CTT
    L   R   R   T   L   E   D   A   E   A   L   F   S   K   Y   C   A   L   T   L
                        E2F         CEBP                        E2F         ATF
241 AAG GAC TAG TTT CGC GCC CTT TCT CAA ATT TAA GCG CGA AAA CTA CGT CAT CTC CAG CGG
    K   D   *                                                                    
              ATF            pVIII protein →
301 CCA CAC CCG GCG CCA GCA CCT GTC AGC GCC ATT ATG AGC AAG GAA ATT CCC ACG CCC
    P   H   P   A   P   A   P   V   S   A   I   M   S   K   E   I   P   T   P
                                                    M   S   K   E   I   P   T   P 361 TAC ATG TGG AGT TAC CAG CCA CAA ATG GGA CTT GCG GCT GGA GCT GCC CAA GAC TAC TCA
    Y   M   W   S   Y   Q   P   Q   M   G   L   A   A   G   A   A   Q   D   Y   S
```

Fig.2 (Cont).

```
421 ACC CGA ATA AAC TAC ATG AGC GGA CCC CAC ATG ATA TCC CGG GTC AAC GGA ATC CGC
    T   R   I   N   Y   M   S   A   G   P   H   M   I   S   R   V   N   G   I   R

481 GCC CAC CGA AAC CGA ATT CTC TTG GAA CAG GCG GCT ATT ACC ACC ACA CCT CGT AAT AAC
    A   H   R   N   R   I   L   L   E   Q   A   A   I   T   T   T   P   R   N   N
                                       NF1
541 CTT AAT CCC CGT AGT TGG CCC GCT GCa CTG GTG TAC CAa GAg AGc CCa GCT CCC ACC ACT
    L   N   P   R   S   W   P   A   A   L   V   Y   Q   E   S   P   A   P   T   T
                                       H4                            NFκB
    NFκB                                                    AP1
601 GTa GTg CTg CCa AGA GAC GCC CAG GCC GAA GTT CAG ATG ACC AAt agc GGG GCG CAG CTT
    V   V   L   P   R   D   A   Q   A   E   V   Q   M   T   N   S   G   A   Q   L
    L1                                          H3              L2
                ATF                                          E3 TATA box
661 GCG GGC TTT aGa CAC AGG GTG CGG TCG CCC GGG CAG GGT ATA ACT CAC CTG ACA ATC
    A   G   F   R   H   R   V   R   S   P   G   Q   G   I   T   H   L   T   I
            H2
                            [E3 transcription start site→
721 AGA GGG CGA ATT CAG CTC AAC GAC GAG TCG GTG AGC TCC TCG CTT GGT CTC CGT CCG
    R   G   R   I   Q   L   N   D   E   S   V   S   S   S   L   G   L   R   P
```

Fig.3.

```
    ...33k protein →
1   GGA GCG CTG CGT CTG GCG CCC AAC GAA CCC GTA TCG ACC CGC GAG CTT AGA AAC AGG ATT
    G   A   L   R   L   A   P   N   E   P   V   S   T   R   E   L   R   N   R   I 61  TTT CCC ACT CTG TAT GCT ATA TTT CAA CAG AGC AGG GGC CAA GAA CAA GAG CTG AAA ATA
    F   P   T   L   Y   A   I   F   Q   Q   S   R   G   Q   E   Q   E   L   K   I 121 AAA AAC AGG TCT CTG CGA TCC CTC ACC CGC AGC TGC CTG TAT CAC AAA AGC GAA GAT CAG
    K   N   R   S   L   R   S   L   T   R   S   C   L   Y   H   K   S   E   D   Q 181                    ←E2 transcription start site]                    E2 TATA box
    CTT CGG CGC ACG CTG GAA GAC GCG GCG CTC TTC AGT AAA TAC TGC GCG CTG ACT CTT
    L   R   R   T   L   E   D   A   A   L   F   S   K   Y   C   A   L   T   L
                E2F            CEBP                        E2F            ATF 241 AAG GAC TAG TTT CGC GCC CTT TCT CAA ATT TAA GCG CGA AAA CTA CGT CAT CTC CAG CGG
    K   D   *
                                                            ATF
301 CCA CAC CCG GCG CCA GCA CCT GTC GTC AGC GCC ATT AGC AAG GAA ATT CCC ACG CCC
    P   Q   P   A   P   A   P   V   V   S   A   I   S   K   E   I   P   T   P
                                                pVIII protein →
                                                        M   S   K   E   I   P   T   P 361 TAC ATG TGG AGT TAC CAG CCA CAA ATG GGA CTT GCG GCT GGA GCT GCC CAA GAC TAC TCA
    Y   M   W   S   Y   Q   P   Q   M   G   L   A   A   G   A   A   Q   D   Y   S
```

Fig.3 (Cont).

```
421
ACC CGA ATA AAC TAC ATG AGC GCG GGA CCC CAC ATG ATA TCC CGG GTC AAC GGA ATC CGC
 T   R   I   N   Y   M   S   A   G   P   H   M   I   S   R   V   N   G   I   R

481                      NF1
GCC CAC CGA AAC CGA ATT CTC TTG GAA CAG GCG GCT ATT ACC ACC ACA CCT CGT AAT AAC
 A   H   R   N   R   I   L   L   E   Q   A   A   I   T   T   T   P   R   N   N

541                                                              NFκB
CTT AAT CCC CGT AGT TGG CCC GCT GCC CTG GTG TAC CAG GAA AGT CCC GCT CCC ACC ACT
 L   N   P   R   S   W   P   A   A   L   V   Y   Q   E   S   P   A   P   T   T
             H4                                          L2

601   NFκB                                          AP1
GTG GTA CTT CCC AGA GAC GCC CAG GCC GAA GTT CAG ATG ACT AAC TCA GGG GCG CAG CTT
 V   V   L   P   R   D   A   Q   A   E   V   Q   M   T   N   S   G   A   Q   L
     L1                                          H3

661                   ATF                                E3 TATA box
GCG GGC TTT CGT CAC AGG GTG CGG TCG CCC GGG CAG GGT ATA ACT CAC CTG ACA ATC
 A   G   F   R   H   R   V   R   S   P   G   Q   G   I   T   H   L   T   I
         H2

721   [E3 transcription start site→
AGA GGG CGA GGT ATT CAG CTC AAC GAC GAG TCG GTG AGC TCC TCG CTT GGT CTC CGT CCG
 R   G   R   G   I   Q   L   N   D   E   S   V   S   S   S   L   G   L   R   P
```

Fig.8(A).
H1299
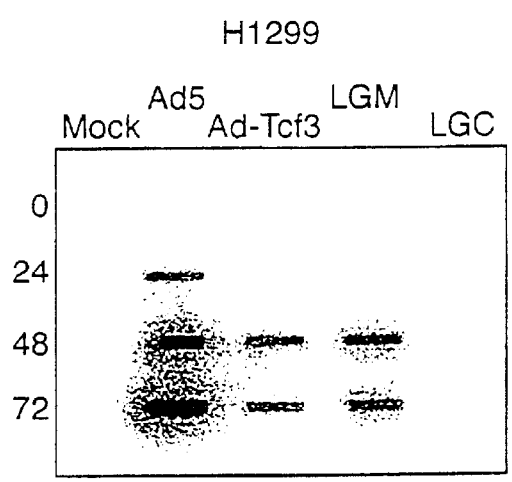
SW480
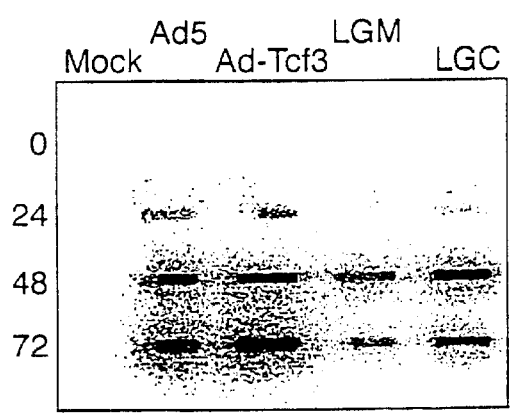
Fig.8(B).
H1299
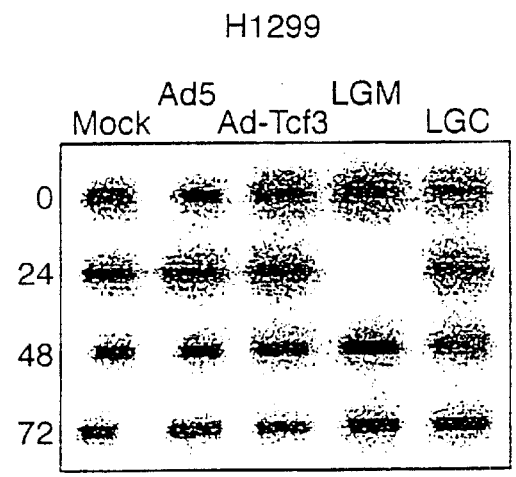
SW480
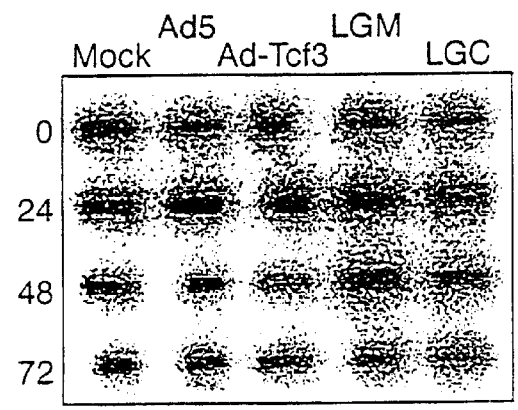

Fig.21.

```
E1B Promoter
                                                                         Sp1 site
         1601                              1631
Ad5      atg taa gtt taa agg gtg aga taa tgt tta act tgc atg gcg tgt taa atg ggg cgg
E1B-Tcf  atg taa gtt taa agg gtg aga taa tgt tta act tgc atg gcg tgt taa atC CCT TTG
                                           E1A polyA site
         1661                              1691
Ad5      ggc tta aag gg* **** **** **** **** **** **** **** **** tat ata
E1B-Tcf  ATC Tta atC CCT TTG ATC Tgg atC CCT TTG ATC Tcc aaC CCT TTG ATC TAG TCC tat ata
                                                                       E1B TATA box
         1721                              1751
Ad5      atg cgc cgt ggg cta atc ttg gtt aca tct gac ctc atg gag gct tgg gag tgt ttg gaa
E1B-Tcf  atg cgc cgt ggg cta atc ttg gtt aca tct gac ctc atg gag gct tgg gag tgt ttg gaa
                     E1B transcription start site
```

ANTI-NEOPLASTIC VIRAL AGENTS

This application is a continuation of Application No. PCT/GB00/01142, filed Mar. 24, 2000, the entire content of which is hereby incorporated by reference in this application.

The present invention provides viral agents that have application in the treatment of neoplasms such as tumours, particularly tumours derived from colon cells, more particularly liver tumours that are metastases of colon cell primary tumours. Still more particularly are provided replication efficient adenovirus constructs that selectively replicate in response to transcription activators present in tumour cells, these factors being present either exclusively or at elevated levels in tumour cells as compared to other cells, and thus which lead to tumour cell death and cell lysis.

By injecting these viral agents locally into the liver it is possible to treat liver metastases; which are a major cause of morbidity in colon cancer patients. Applications beyond this, e.g. to other sites and other tumours, such as colorectal cancers and melanomas, are also provided.

Colon cancer presents with locally advanced or metastatic disease in the majority of patients. Most patients are left with liver metastases as the only site of disease after resection of the primary tumour. Partial liver resection only cures about 10% of patients, while in patients with multiple metastases in both liver lobes resection is not feasible and loco-regional or systemic treatment with chemotherapy is indicated (Labianca et al., 1997). Systemic chemotherapy with 5-fluorouracil and leucovorin or irinotecan will produce response rates of only 20% (Cunningham et al., 1998; Stupp et al., 1998).

Locoregional chemotherapy of the liver has been explored for over 15 years. Most liver metastases are supplied with blood by the hepatic artery, so intra-arterial hepatic chemotherapy (IAHC) allows for much higher exposure of the metastases to cytotoxic drugs. The high extraction rate of normal liver decreases the systemic drug concentration resulting in less toxicity with IAHC having been shown repeatedly to give response rates over 60% (Kemeny et al., 1987; Kemeny et al., 1992; Patt and Mavligit, 1991).

Specific defects in tumour cells make it possible to devise rational strategies for targeting tumour cells without harming normal cells. With the exception of anti-angiogenic therapy, this usually requires introduction of exogenous DNA into tumour cells, and the most efficient way to do this is with viruses. For example, U.S. Pat. No. 5,698,443 describes a tumour specific adenovirus that is targeted at prostate cancer cells. This virus utilises a prostate specific enhancer sequence driving the viral E1 genes and the patent suggests its use to express toxins specifically in the target cell.

Viruses which replicate selectively in tumour cells have great potential for gene therapy for cancer. In principle, selectively replicating cytotoxic viruses can spread progressively through a tumour until all of its cells are destroyed. This overcomes the need to infect all tumour cells at the time the virus is injected, which is a major limitation to conventional replacement gene therapy, because in principle virus goes on being produced, lysing cells on release of new virus, until no tumour cells remain. An important fundamental distinction in cancer gene therapy is thus between single hit approaches, using non-replicating viruses, and multiple hit approaches, using replicating viruses.

Single hit approaches work by directly transducing tumour cells with toxic genes; ignoring bystander effects, one virus particle kills one cell. Examples include restoration of tumour suppressor gene expression and conditional expression of toxins using tumour-specific promoters. For single hit approaches the amount of virus injected is an important limiting factor. Multiple hit approaches circumvent this limitation either by provoking an immune reaction against tumour cells, or by using viruses that replicate within the tumour. Since the majority of tumour cells are not killed by the injected virus itself, the amount of virus injected should not be an important factor limiting the therapeutic response.

Classic gene replacement therapy has been performed with retroviruses expressing p53 (Roth et al., 1996). Since p53 can be converted to its oncogenic form by mutations at over 500 sites in the open reading frame (Flaman et al., 1994), retroviral replication will convert at least 1% of the transduced p53 to such undesired mutant form. This means that each patient received around 25 million infectious units of virus expressing mutant p53 (Estreicher and Iggo, 1996).

A more promising approach expressing wild type p53 using an adenovirus, Ad-CMV-p53, has been demonstrated clinically in head and neck cancer and is currently under investigation in lung, colon and liver cancer (Clayman et al., 1998). Adenoviruses are relatively stable, can be produced at high titres, and can infect both quiescent and dividing cells of many different types. Overall, Ad-CMV-p53 appears exceptionally non-toxic but probably ineffective as a single agent; hence, there is a place for more aggressive second generation viruses.

Further target specific defects are mutations of p16, cdk4, cyclin D or Rb (Bartek et al., 1997) in the retinoblastoma pathway which cause loss of G1/S control and essentially all tumours have these. The only significant exception is colon cancer, where mutations in the Rb pathway itself are rare. The net result of these defects is increased E2F activity, which means that tumours can be selectively targeted by viruses expressing toxic genes from E2F-regulated promoters. This has been demonstrated using an adenovirus expressing the HSV thymidine kinase gene from such a promoter (Parr et al., 1997); cells containing Rb-pathway mutations express tk and can be killed by ganciclovir. Such an approach relies on an increase in the activity of specific transcription factors in tumour cells.

The rational basis for tumour targeting is better understood for non-replicating E2F-targeting viruses than it is for p53, but both are still single hit approaches and it is very difficult to see how they can ever be used for more than treatment of local disease. The tumour burden in late stage disease is around $10^{12}$ cells, so while at an effective multiplicity of infection of one treatment would be feasible, in practice biodistribution and receptor problems mean that many orders of magnitude higher multiplicities are required.

One elegant way to circumvent this limitation is to recruit the immune system to kill the tumour cells. The role of the gene therapy virus is simply to provoke or reinforce the immune response. There is abundant evidence that tumours express new antigens, but in cancer patients the immune system has clearly failed to prevent tumour formation. Many currently attempted techniques target single antigens, eg production of cytotoxic T cells against MAGE antigens in melanoma, but the goal for therapy must be to induce a simultaneous response against multiple different antigens, because genetic instability in tumours means targeting of single antigens is unlikely to produce lasting responses because the number of tumour cells exceeds the mutation rate. Hence acquired resistance to immunotherapy is common.

An attractive solution to the single hit problem is to produce virus within the tumour. This can be achieved by injecting retroviral producer cell lines into the tumour bed, a strategy currently being tested in a clinical trial for glioblastoma (reviewed by Roth and Cristiano, 1997). This is an elegant but limited approach as it relies on immune privilege in the CNS to avoid immediate rejection of the grafted cells, and tumour targeting depends on the fact that retroviruses do not infect non-dividing normal brain cells. It falls short of the goal of tumour cell-specific viral replication because the viruses produced are not themselves replication competent and virus production is dependent on survival of the packaging cells rather than the presence of tumour cells.

The prototype tumour selective virus is a defective adenovirus lacking the E1B 55K gene (dl 1520ONYX 015, Bischoff et al., 1996). In normal adenoviruses 55K inactivates p53, hence it should not be required in cells where p53 is mutant. In practice, many cells containing wild type p53 are killed by the virus (Heise et al., 1997). The present inventors have tested this in H1299 p53-null lung carcinoma cells containing wild type p53 under a tetracycline-regulated promoter and found that dl 1520 replicates as well in the presence as in the absence of wild type p53. Besides targeting p53, E1B 55K is required for selective viral RNA export (Shenk, 1996) and it is not immediately obvious how loss of p53 could substitute for this function. At present there is no convincing evidence that dl 1520 targets p53 defects (Goodrum 1997, Goodrum 1998, Hall 1998, Rothman 1998, Turnell 1999).

As with p53-expressing viruses, combination therapy with chemotherapy and dl 1520 gives better results both in vitro and in xenografts (Heise et al., 1997). In principle, the virus should undergo multiple rounds of replication until there are no tumour cells remaining and since each infected cell produces $10^3$ to $10^4$ new virus particles, the amount of input virus should not be limiting. In practice, the required amount of dl 1520 virus injected is comparable for therapy with Ad-CMV-p53. This means that the virus is not performing as expected for a replicating virus with the reasons for this again probably quite complex. Adenoviruses normally produce superficial mucosal infections which are spread by droplets containing infected cells. Infected cells retain progeny virus. Lack of effective virus release from lysed cells will militate against the production of deep, spreading infection, which is the goal if virus is to penetrate to all parts of the tumour.

Rational targeting of E2F defects is complicated by the fact that as part of its life cycle the adenovirus already produces proteins (E1A and E4 orf 6/7) which target E2F. Since E1A and orf 6/7 are multifunctional proteins the effect of E1A and orf 6/7 mutations is complex and unpredictable.

In addition to E2F and p53, there are four transcription factors whose activity is known to increase in tumours. They are Tcf4, RBPJκ and Gli-1, representing the endpoints of the wnt, notch and hedgehog signal transduction pathways (Dahmane et al., 1997; Jarriault et al., 1995; van de Wetering et al., 1997) and HIF1 alpha, which is stabilised by mutations in the Von Hippel Lindau tumour suppressor gene (Maxwell et al 1999). Mutations in APC or β-catenin are universal defects in colon cancer (Korinek et al., 1997; Morin et al., 1997); but they also occur at lower frequency in other tumours, such as melanoma (Rubinfeld et al., 1997). Such mutations lead to increased Tcf activity in affected cells. The hedgehog pathway is activated by mutations in the patched and smoothened proteins in basal cell cancer (Stone et al., 1996; Xie et al., 1998). Notch mutations occur in some leukaemias (Ellisen et al., 1991). Telomerase activation is one of the hallmarks of cancer (Hanahan D. and Weinberg RA. The hallmarks of cancer. Cell. 100, 57–70, 2000) and results from increased activity of the telomerase promoter, although the mechanism is unknown. According to Cong Y S et al (1999, HMG 8, 137–42) the elements responsible for promoter activity are contained within a region extending from 330 bp upstream of the ATG to the second exon of the gene and thus this sequence is a further suitable promoter sequence for use in the viral constructs and viruses of the invention.

The present inventors have now designed and produced viral DNA constructs, and replicating viruses encoded thereby, preferably in the form of recombinant viral constructs and viruses, which rationally target known causal oncogenic transcription defects in tumours by using these to control transcription of one or more early viral genes encoding for proteins which are mechanistically directly involved in viral nucleic acid replication (for examples of such genes see eg. DePamphilis, M L, Concepts in Eukaryotic DNA Replication pp 481–484 and 488–491, 1999 Cold Spring Harbor Laboratory Press, New York which is incorporated herein by reference). Preferably these viral genes are selected from the group consisting of polymerase, primase, nuclease, helicase, ligase, terminal protein and nucleic acid binding protein genes. Preferred enzymatic products of five of these genes are classified in the following Enzyme Commission classifications: polymerase (EC 2.7.7.7), primase (EC 2.7.7.6), nuclease (EC 3.1.11-25), helicase (EC 3.6.1.3) and ligase (EC 6.5.1.1-2). These classifications may vary, for example, in parvoviruses, eg. Adenoassociatedviruses (AAV), they include NS1/Rep proteins, which have nuclease and helicase activities essential for replication In the preferred constructs and viruses produced by the inventors these genes are particularly the viral DNA polymerase, viral DNA terminal protein and/or viral DNA binding protein genes. Preferred viruses are those having E1, E2 and E3 viral transcription units, such as adenoviruses. It is particularly preferred that at least the E2 transcription unit of the virus is altered such that it is made responsive to factors that are present at increased levels or increased activity, or are only present in, a target tumour cell. Rittner et al (J. Virol (1997) p 3307–3311) teach that it is not possible to manipulate the E2 promoters close to the cap sites because of the overlap with the major late open reading frame L4. The present inventors however find that this manipulation is indeed possible with advantageous results.

It has thus been determined that by controlling nucleic acid replication capability, rather than factors such as RNA export capability or toxicity due to insertion of recombinant genes, the inventors can provide selectivity of cytotoxic effect to tumour cells.

Most importantly and advantageously, the present inventors have made possible to target tumour cells with a virus encoding only wild type viral proteins, whose expression is specifically regulated by transcription factors preferentially or exclusively activated in tumour cells. Preferred virus encodes a full set of wild type proteins. Such virus can be used to better effect than prior art viral agents which have relied on mutation of viral proteins or targeting of cells of a particular tissue origin, eg. prostate.

Thus in a first aspect of the present invention there is provided a viral DNA construct encoding for a virus that is capable of replication in a human or animal tumour cell type and causing tumour cells of that type to die characterised in that the construct comprises one or more selected transcription factor binding sites together with, and operatively positioned such as to promote expression of, open reading frames encoding early viral proteins, the protein products of those reading frames being mechanistically directly involved in viral construct nucleic acid replication wherein the selected transcription factor binding sites are for a transcription factor the level or activity of which is increased in a human or animal tumour cell relative to that of a normal human or animal cell of the same type.

Preferred constructs of the invention have a nucleic acid sequence corresponding to that of a wild type virus sequence characterised in that it has one or more wild type transcription factor binding sites replaced by one or more selected transcription factor binding sites, these sites being operatively positioned in the promoter region which controls expression of early genes such as to promote expression of the open reading frame of the gene, the protein products of those genes being mechanistically directly involved in viral nucleic acid replication wherein the selected transcription factor binding sites are for a transcription factor the level or activity of which is increased in a human or animal tumour cell relative to that of a normal human or animal cell of the same type.

Preferably the viral DNA construct is characterised in that the sites which replace the wild type transcription factor sites controlling expression of said early genes are for a transcription factor whose activity or level is specifically increased by causal oncogenic mutations.

While the controlled open reading frames or genes may be one or more of the viral polymerase, primase, nuclease, helicase and ligase, preferably they are one or more of the DNA polymerase, DNA terminal protein and/or DNA binding protein. More preferably the construct or virus is such that it has E1, E2 and E3 regions and the tumour specific transcription factor binding site replaces one or more wild type E2 transcription factor binding sites.

Preferably the viral DNA construct is characterised in that it encodes a functional viral RNA export capacity. For adenovirus this is encoded in the E1 and E4 regions, particularly the E1B 55K and E4 orf 6 genes. Thus preferably the encoded virus is of wild type with respect to expression of these genes in tumour cells. Most preferably the E1B 55K and E4 orf 6 open reading frames are functional and/or intact where present in the corresponding wild type virus.

It will be realised by those skilled in the art that any virus which is potentially cytotoxic to tumour cells may be employed in producing viral constructs of the present invention. Particularly examples may include adenovirus, lentivirus, polyoma virus, vaccinia virus, herpesvirus and parvovirus. Preferably the virus is an adenovirus, more preferably an adenovirus that is of high specificity for a target tumour cell type, eg. for a colon tumour type.

Preferred colon tumour specific adenoviruses are encoded by viral DNA constructs corresponding to the DNA sequence of Ad5 or one or more of the enteric adenoviruses Ad40 and Ad41 modified as described above. Ad40 and Ad41, which are available from ATCC, are selective for colon cells and one important difference to Ad5 is that there is an additional fibre protein. The fibre protein binds to the cell surface receptor, called the coxsackie-adeno receptor or CAR for Ad5. Colon cells have less CAR than lung cells which Ad5 is adapted to infect. Ad40 and Ad41 have two fibre proteins, with the possibility being that they may use two different receptors. The expected form of resistance to virus therapy is loss of the receptor, which obviously prevents infection. Genetic instability in tumours means this will happen at some reasonable frequency; about 1 in 100 million cells, a mutation rate of 1 in $10^8$. If you have to delete two receptors you multiply the probabilities; ie. loss of both will occur in 1 in $10^{16}$ cells. A tumour contains between $10^9$ and $10^{12}$ cells. Hence resistance is less likely to develop if a virus uses more than one receptor. One fibre protein in Ad40 and 41 uses CAR whilst the receptor used by the other is as yet unknown.

Advantageously the use of the constructs of the invention, particularly in the form of viruses encoded thereby, to treat liver metastasis is relatively non-toxic compared to chemotherapy, providing good spread of virus within the liver aided by effective replication.

Preferred viral constructs of the invention are derived from adenovirus or parvovirus genomic DNA, more preferably adenovirus genomic DNA, and are mutated such that transcription of essential viral genes encoded by the E2 viral transcription unit is made dependent on the presence of oncogenic mutations in tumour cells. Preferably only cells containing these oncogenic mutations can activate transcription of the viral E2 genes. Since the E2 unit encodes the viral DNA polymerase, DNA terminal protein and DNA binding protein, the virus can only replicate in tumour cells. It is preferred that the E2 early promoter transcription factor binding site is replaced by the tumour cell specific transcription factor binding site.

Preferred tumour specific transcription factor binding sites that are used in place of wild type sites are those described above as Tcf-4, HIF1alpha, RBPJκ and Gli-1 sites, and a fragment of the telomerase promoter conferring tumour-specific transcription. A most preferred transcription factor binding site is that which binds Tcf-4, such as described by Vogelstein et al in U.S. Pat. No. 5,851,775 and is responsive to the heterodimeric β-catenin/Tcf-4 transcription factor. As such the transcription factor binding site increases transcription of genes in response to increased β-catenin levels caused by APC or β-catenin mutations. The telomerase promoter is described by Wu K J. et al (1999, Nat Genet 21, 220–4) and Cong Y S. et al (1999 HumMol Genet 8, 137–42). A further preferred binding site is that of HIF1alpha, as described by Maxwell P H. et al, (1999 Nature 399, 271–5). One may use a HIF1alpha-regulated virus to target the hypoxic regions of tumours, involving no mutation of the pathway as this is the normal physiological response to hypoxia, or the same virus may be used to target cells with VHL mutations either in the familial VHL cancer syndrome, or in sporadic renal cell carcinomas, which also have VHL mutations. A retrovirus using the HIF promoter to target hypoxia in ischemia has already been described by Boast K. et al (1999 Hum Gene Ther 10, 2197–208).

Particularly the inventors have now provided viral DNA constructs, and viruses encoded thereby, which contain the Tcf transcription factor binding sites referred to above in operational relationship with the early gene open reading frames described above, particularly in place of wild type transcription factor binding sites in the E2 promoter and shown that these are selective for tumour cells containing oncogenic APC and β-catenin mutations. Tcf-4 and its heterodimer bind to a site designated Tcf herein. Preferred such replacement sites are single or multiples of the Tcf binding sequence, eg. containing 2 to 20, more preferably 2 to 6, most conveniently, 2, 3 or 4 Tcf sites.

Particular Tcf sites are of consensus sequence (A/T)(A/T)CAA(A/T)GG, see Roose, J., and Clevers, H. (1999 Biochim Biophys Acta 1424, M23–37), but are more preferably as shown in the examples herein.

More preferred viral constructs and viruses of the invention are those having E3 domains and are characterised in that they have mutations to one or more residues in the NF1, NFκB, AP1 and/or ATF regions of the E3 promoter, more preferably those mutations which reduce E2 gene transcription caused by E3 promoter activity. The present inventors have particularly provided silent mutations, these being such as not to alter the predicted protein sequence of any viral protein, which alter the activity of key viral promoters.

NFκB is strongly induced in regenerating liver cells, ie. hepatocytes (see Brenner et al J. Clin. Invest. 101 p802–811). Liver regeneration to fill the space vacated by the tumour is likely to occur following successful treatment of metastases. In addition, if one wishes to treat hepatoma, which arise on a background of dividing normal liver cells, then destroying the NFκB site is potentially advantageous.

In a preferred embodiment of the first aspect of the present invention the inventors have replaced a short region in the E2 early promoter, which is not overlapped by coding sequence, with multiple Tcf binding sites, more preferably 3 or 4 such sites, and most preferably 4 sites. One resulting preferred viral construct and encoded virus are referred to herein as Ad-Tcf3, having 3 such sites, and the virus expresses E2 gene products and replicates better in colon than in lung tumour cells (see Examples). This shows that mutations of the type described can modify the activity of the E2 promoter in the desired way without untoward effects on other aspects of the viral life cycle. This is not obvious a priori because, as well as encoding the E2 promoter, this region is transcribed and retained in the 5'-untranslated region of the pVIII protein RNA, it is transcribed but spliced out of the L5 late RNA and it forms part of the 3'-untranslated region of the 33k protein RNA.

Although Ad-Tcf3 replicates better in colon than lung tumour cells, the difference is only around ten-fold. LGC, a virus of the invention combining the E2 mutations in Ad-Tcf with an E1B 55K deletion, shows around 1000-fold selectivity for colon cancer cells. This demonstrates that E2 promoter activity can be made limiting for viral replication, because the identical virus with the normal E2 promoter (LGM) shows no specificity for colon cells. For a colon-targeting strategy this is an important result because it means a colon-specific virus can be made by titrating the E2 promoter activity.

The probable explanation for the selectivity of LGC is that the E1B 55k protein is required for nuclear export of late viral RNAs, including the E2 DBP late RNA, and that the E2 RNA export defect in E1B 55K-deficient viruses can be overcome by increasing E2 RNA production by inserting Tcf sites in place of the normal transcription factor binding sites in the E2 promoter.

One method for increasing the specificity of the AdTcf3, and similar 3xTcf driven E2 viruses of the invention for colon tumours is to reduce its E2 promoter activity in non-colon cells. One possible way to do this is to alter the number of Tcf sites. Reduction in the number of Tcf sites to two could reduce non-specific leakiness, but since Tcf promoters are actively repressed in non-colon cells by groucho (Fisher and Caudy, 1998) and acetylation (Waltzer 1998) it is more likely that increasing the sites will give a more tightly regulated promoter as the more sites there are the more repressor will be bound in non-colon cells. E1A normally activates the E2 promoter through the ATF site. In the absence of such targeting E1A represses promoters, eg. by chelating p300/CBP. Since the ATF site is deleted in the Tcf-mutant E2 promoter, E1A produced by the virus should reduce general leakiness of the mutant E2 promoter in all cell types. The E3 promoter is back-to-back with the E2 promoter and the distinction between them is defined but functionally arbitrary. Hence further reduction of the activity of the mutant E2 promoter is possible by modifying or deleting transcription factor binding sites in the E3-promoter. Since the E3 promoter lies in coding sequence it cannot just be deleted. Instead the inventors have provided up to 16 silent substitutions changing critical residues in known NF1, NFκB, AP1 and ATF sites (Hurst and Jones, 1987, Genes Dev 1, 1132–46, incorporated herein by reference).

Further viral constructs of the present invention may be provided by modifying the E2-late promoter of adenoviruses. The E2-early promoter controls transcription of DNA polymerase (pol), DNA binding protein (DBP) and preterminal protein (pTP). By mutating the E2 late promoter it is possible to have a similar effect, ie. at least in part, to the E1B deletion because E1B deletion reduces export of DBP RNA expressed from the E2 late promoter. DBP is required stoichiometrically for DNA replication, so reducing DBP production in normal cells is desirable. Since the E2 late promoter lies in 100k protein coding sequence it cannot just be deleted. Instead the inventors have determined that it can inactivated with silent mutations changing critical residues in known transcription factor binding sites.

Particular transcription factor binding sites in the E2 late promoter were identified by DNase I footprinting (marked I–IV in FIG. 4 herein; Goding et al, 1987, NAR 15, 7761–7780). The most important is a CCAAT box lying in footprint II. Mutation of this CCAAT box reduces E2 late promoter activity 100-fold in CAT assays (Bhat et al, 1987, EMBO J, 6,2045–2052). One such mutation changes the marked CCAAT box sequence GAC CAA TCC to GAT CAG TCC. (see FIG. 4 below). This is designed to abolish binding of CCAAT box binding factors without changing the 100k protein sequence. Additional silent mutations in the other footprints can be used to reduce activity further.

An alternative or additional mutation possible is to regulate expression of E1B transcription by mutating the E1B promoter. This has been shown to reduce virus replication using a virus in which a prostate-specific promoter was used to regulate E1B transcription (Yu, D. C., et al 1999 Cancer Research 59, 1498–504). A further advantage of regulating E1B 55K expression in a tumour-specific manner would be that the risk of inflammatory damage to normal tissue would be reduced (Ginsberg, H. S., et al 199 PNAS 96, 10409–11). The inventors have produced viruses with Tcf sites replacing the E1B promoter Sp1 site to test this proposition.

Further embodiments include the following possible modifications. To further restrict replication one can insert further tumour specific, eg. Tcf, sites in the E1A promoter. To achieve regulation by inserting short oligonucleotides, one must delete the existing regulatory sequences in the E1A promoter. This requires simultaneous mutation of both inverted terminal repeats and transfer of the packaging signal elsewhere, eg. to the E4 region. In contrast with, for example, the Calydon viruses, the design of the present inventors viruses means that, despite retaining a full complement of adenoviral genes, spare packaging capacity is available, which can be used to express conditional toxins, such as the prodrug-activating enzyme HSV thymidine kinase (tk). This could be expressed for example from the E3 promoter, whose activity is regulated in some of the viruses, to provide an additional level of tumour targeting. Alternatively, it could be expressed from a constitutive promoter to act as a safety feature, since ganciclovir would then be able to kill the virus. Constitutive tk expression in an E1B-deficient virus also increases the tumour killing effect, albeit at the expense of replication (Wildner, O., et al 1999 Gene Therapy 6, 57–62). An alternative prodrug-activating enzyme to express would be cytosine deaminase (Crystal, R.

G., et al 1997 Hum Gene Ther 8, 985–1001), which converts 5FC to 5FU. This has advantage because 5FU is one of the few drugs active on liver metastases, the intended therapeutic target, but produces biliary sclerosis in some patients.

The amino-terminus of E1A contains a region of E1A that binds p300, a histone acetylase which functions as a general transcription factor. One way E1A activates genes is by bringing p300 to the promoter. To do this E1A binds transcription factors like ATF. Hence E1A activates promoters that contain ATF sites. Virus vMB13 herein retains the ATF site in the E3 promoter providing advantage in this respect. The problem is that if a promoter does not have an ATF site, E1A will repress it by binding p300. This is what happens with p53, for example: E1A blocks p53-dependent transcription in a manner that requires the p300 binding site in E1A. Tcf repression by E1A is a possibility in some cell lines, so mutation of the E1A p300-binding site may be preferred for such treatment.

The present inventors see a difference between vMB13 and vMB14 in HCT 116 cells, where the only difference between the two viruses is in the ATF site in the E3 promoter. Thus mutation of the E1A p300-binding site in vMB14 might be advantageous. Alternatively, the difference could be due to direct activation of the ATF site because Xu L et al (2000, Genes Dev 14, 585–595) report that ATF/CREB sites can be activated by wnt signals, although the mechanism is unknown.

Having produced a virus with one or more levels of regulation to prevent or terminate replication in normal cells, it is further preferred and advantageous to improve the efficiency of infection at the level of receptor binding. The normal cellular receptor for adenovirus, CAR, is poorly expressed on some colon tumour cells. Addition of a number of lysine residues, eg 15 to 25, more preferably about 20, to the end of the adeno fibre protein (the natural CAR ligand) allows the virus to use heparin sulphate glycoproteins as receptor, resulting in more efficient infection of a much wider range of cells. This has been shown to increase the cytopathic effect and xenograft cure rate of E1B-deficient viruses (Shinoura, H., et al 1999 Cancer Res 59, 3411–3416 incorporated herein by reference).

A n alternative strategy is to incorporate the cDNA encoding for Ad40 and/or Ad41 fibres into the construct of the invention as described above. The EMBL and Genbank databases list scuh sequences and they are further described in Kidd et al Virology (1989) 172(1), 134–144; Pieniazek et al Nucleic Acids Res. (1989) November 25; 17–20, 9474; Davison et al J. Mol. Biol (1993) 234(4) 1308–16; Kidd et al Virology (1990) 179(1) p139–150; all of which are incorporated herein by reference.

In a second aspect of the invention there is provided the viral DNA construct of the invention, particularly in the form of a virus encoded thereby, for use in therapy, particularly in therapy of patients having neoplasms, eg. malignant tumours, particularly colorectal tumours and most particularly colorectal metastases. Most preferably the therapy is for liver tumours that are metastases of colorectal tumours.

In a third aspect there is provided the use of a viral DNA construct of the invention, particularly in the form of a virus encoded thereby, in the manufacture of a medicament for the treatment of neoplasms, eg. malignant tumours, particularly colorectal tumours and most particularly colorectal metastases. Most preferably the treatment is for liver tumours that are metastases of colorectal tumours.

In a fourth aspect of the invention there are provided compositions comprising the viral DNA construct of the invention, particularly in the form of a virus encoded thereby, together with a physiologically acceptable carrier. Such carrier is typically sterile and pyrogen free and thus the composition is sterile and pyrogen free with the exception of the presence of the viral construct component or its encoded virus. Typically the carrier will be a physiologically acceptable saline.

In a fifth aspect of the invention there is provided a method of manufacture of the viral DNA construct of the invention, particularly in the form of a virus encoded thereby comprising transforming a viral genomic DNA, particularly of an adenovirus, having wild type transcription factor binding sites, particularly as defined for the first aspect, controlling transcription of genes the protein products of which are directly mechanistically involved in viral nucleic acid replication, such as to operationally replace these sites by tumour specific transcription factor binding sites, particularly replacing them by Tcf transcription factor binding sites. Operational replacement may involve partial or complete deletion of the wild type site. Preferably the transformation inserts two or more, more preferably 3 or 4, Tcf-4 transcription factor binding sites. More preferably the transformation introduces additional mutations to one or more residues in the NF1, NFκB, AP1 and/or ATF binding sites in the E3 promoter region of the viral genome. Such mutations should preferably eliminate interference with E2 activity by E3 and reduce expression of E2 promoter-driven genes in normal cells and non-colon cells. Reciprocally, it preferably replaces normal regulation of E3 with regulation by Tcf bound to the nearby E2 promoter.

Traditional methods for modifying adenovirus require in vivo reconstitution of the viral genome by homologous recombination, followed by multiple rounds of plaque purification. The reason for this is the difficulty of manipulating the 36kb adenovirus genome using traditional cloning techniques. Newer approaches have been developed which circumvent this problem, particularly for E1-replacement vectors. The Transgene and Vogelstein groups use gap repair in bacteria to modify the virus (Chartier et al., 1996; He et al., 1998). This requires the construction of large vectors which are specific for each region to be modified. Since these vectors are available for E1-replacement, these approaches are very attractive for construction of simple adenoviral expression vectors. Ketner developed a yeast-based system where the adenoviral genome is cloned in a YAC and modified by two step gene replacement (Ketner et al., 1994). The advantage of the YAC approach is that only very small pieces of viral DNA need ever be manipulated using conventional recombinant DNA techniques. Conveniently, a few hundred base pairs on either side of the region to be modified are provided and on one side there should be a unique restriction site, but since the plasmid is very small this is not a problem. The disadvantage of the Ketner approach is that the yield of YAC DNA is low.

The present inventors have combined the bacterial and yeast approaches. Specifically, they clone the viral genome by gap repair in a circular YAC/BAC in yeast, modify it by two step gene replacement, then transfer it to bacteria for production of large amounts of viral genomic DNA. The latter step is useful because it permits direct sequencing of the modified genome before it is converted into virus, and the efficiency of virus production is high because large amounts of genomic DNA are available. They use a BAC origin to avoid rearrangement of the viral genome in bacteria. Although this approach has more steps, it combines all of the advantages and none of the disadvantages of the pure bacterial or yeast techniques.

Although it can be used to make E1-replacement viruses, and the inventors have constructed YAC/BACs allowing cycloheximide selection of desired recombinants in the yeast excision step to simplify this task, the main strength of the approach is that it allows introduction of mutations at will throughout the viral genome. Further details of the YAC/BAC are provided by the inventors as their contribution to Gagnebin et al (1999) Gene Therapy 6, 1742–1750) which is incorporated herein by reference. :Sequential modification at multiple different sites is also possible without having to handle large DNA intermediates in vitro.

The adenovirus strain to be mutated using the method of the invention is preferably a wild type adenovirus. Conveniently adenovirus 5 (Ad 5) is used, as is available from ATCC as VR5. The viral genome is preferably completely wild type outside the regions modified by the method, but may be used to deliver tumour specific toxic heterologous genes, eg. p53 or genes encoding prodrug-activating enzymes such as thymidine kinase which allows cell destruction by ganciclovir. However, the method is also conveniently applied using viral genomic DNA from adenovirus types with improved tissue tropisms (eg. Ad40 and Ad41).

In a sixth aspect of the present invention there is provided a method for treating a patient suffering from neoplasms wherein a viral DNA construct of the invention, particularly in the form of a virus encoded thereby, is caused to infect tissues of the patient, including or restricted to those of the neoplasm, and allowed to replicate such that neoplasm cells are caused to be killed.

The present invention further attempts to improve current intra-arterial hepatic chemotherapy by prior administration of a colon-targeting replicating adenovirus. DNA damaging and antimetabolic chemotherapy is known to sensitise tumour cells to another replicating adenovirus in animal models (Heise et al., 1997). For example, during the first cycle the present recombinant adenovirus can be administered alone, in order to determine toxicity and safety. For the second and subsequent cycles recombinant adenovirus can be administered with concomitant chemotherapy. Safety and efficacy is preferably evaluated and then compared to the first cycle response, the patient acting as his or her own control.

Route of administration may vary according to the patients needs and may be by any of the routes described for similar viruses such as described in U.S. Pat. No. 5,698,443 column 6, incorporated herein by reference. Suitable doses for replicating viruses of the invention are in theory capable of being very low. For example they may be of the order of from $10^2$ to $10^{13}$, more preferably $10^4$ to $10^{11}$, with multiplicities of infection generally in the range 0.001 to 100.

For treatment a hepatic artery catheter, eg a port-a-cath, is preferably implanted. This procedure is well established, and hepatic catheters are regularly placed for local hepatic chemotherapy for ocular melanoma and colon cancer patients. A baseline biopsy may be taken during surgery.

A typical therapy regime might comprise the following:
Cycle 1: adenovirus construct administration diluted in 100 ml saline through the hepatic artery catheter, on days 1, 2 and 3.
Cycle 2 (day 29): adenovirus construct administration on days 1, 2, and 3 with concomitant administration of FUDR 0.3 mg/kg/d as continuous infusion for 14 days, via a standard portable infusion pump (e.g. Pharmacia or Melody), repeated every 4 weeks.

Toxicity of viral agent, and thus suitable dose, may be determined by Standard phase I dose escalation of the viral inoculum in a cohort of three patients. If grade III/IV toxicity occurs in one patient, enrolment is continued at the current dose level for a total of six patients. Grade III/V toxicity in ≧50% of the patients determines dose limiting toxicity (DLT), and the dose level below is considered the maximally tolerated dose (MTD) and may be further explored in phase II trials.

It will be realised that GMP grade virus is used where regulatory approval is required.

It will be realised by those skilled in the art that the administration of therapeutic adenoviruses may be accompanied by inflammation and or other adverse immunological event which can be associated with eg. cytokine release. Some viruses according to the invention may also provoke this, particularly if E1B activity is not attenuated. It will further be realised that such viruses may have advantageous anti-tumour activity over at least some of those lacking this adverse effect. In this event it is appropriate that an immunosuppressive, anti-inflammatory or otherwise anti-cytokine medication is administered in conjunction with the virus, eg, pre-, post- or during viral adminstration. Typical of such medicaments are steroids, eg, prednisolone or dexamethasone, or anti-TNF agents such as anti-TNF antibodies or soluble TNF receptor, with suitable dosage regimes being similar to those used in autoimmune therapies. For example, see doses of steroid given for treating rheumatoid arthritis (see WO93/07899) or multiple sclerosis (WO93/10817), both of which in so far as they have US equivalent applications are incorporated herein by reference.

The present invention will now be described by way of illustration only by reference to the following non-limiting Sequences, Figures and Examples. Further embodiments falling within the scope of the claims will occur to those skilled in the art in the light of these.

Sequence Listing

SEQ ID No 1 is the DNA sequence of Ad 5 with the E2 and E3 transcription site mutated in accordance with the invention as shown in FIG. 2 with 4xTcf inserted in place of wild type E2 promoter.

SEQ ID No 2 is the partial amino acid sequence of the 33k protein encoded in SEQ ID No 1 unaffected by the insertion of Tcf instead of the wild type E2 promoter.

SEQ ID No 3 is the partial amino acid sequence of the pVIII protein encoded in SEQ ID No 1 unaffected by the insertion of Tcf instead of the wild type promoter.

SEQ ID No 4 is of wild type Adenovirus VR5 in the E2/E3 region.

SEQ ID No 5 is the DNA sequence of E2 late promoter as changed in a preferred virus of the invention as shown in FIG. 4.

SEQ ID No 6 is a partial amino acid sequence 100k protein encoded in SEQ ID No 5 that is unaffected by the mutations in the late promoter.

SEQ ID No 7 is the DNA sequence of E1B promoter as mutated in a preferred virus of the invention as shown in FIG. 20.

SEQ ID No 8 is that of a part of the telomerase promoter site that may be used in place of the Tcf sites exemplified herein.

SEQ ID No 9 to 25 are of primers G61 to G101 set out in the experimental herein.

SEQ ID No 26 is that of a single Tcf binding site.

SEQ ID No 27 is that of 2 Tcf sites and flanking adenoviral DNA as found in a preferred virus described herein.

SEQ ID No 28 is that of a mutant 3 Tcf site sequence with flanking viral DNA and an inactive Tcf site.

SEQ ID No 29 is that of a mutant 4 Tcf site sequence with flanking viral DNA as used in preferred viruses of the invention.

SEQ ID No 30 and 31 are forward and reverse primers for mutating the E1B promoter in a preferred virus of the invention.

SEQ ID No 32, 33 and 34 are forward and reverse primers and a probe respectively for quantitative PCR measurement of E2 expression in Taqman protocol.

SEQ ID No 35, 36 and 37 are forward and reverse primers and a probe respectively for quantitative PCR measurement of E3 expression in Taqman protocol.

SEQ ID No 38, 39 and 40 are forward and reverse primers and a probe respectively for quantitative PCR measurement of E1B expression in Taqman protocol.

SEQ ID No 41, 42 and 43 are forward and reverse primers and a probe respectively for quantitative PCR measurement of E4 expression in Taqman protocol.

SEQ ID No 44 and 45 are forward and reverse primers for fibre expression measurement.

Sequences are also provided in the Example and figures below showing primers and end construct virus sequences and their features of interest.

FIGURES

FIG. 1 shows wild type E2 region position where transcription factor sites are inserted in preferred adenoviruses of the invention (SEQ ID NO:46).

FIG. 2 shows E3 region changes to wild type virus in a preferred virus (SEQ ID NO:47).

FIG. 3 shows E2/E3 region of wild type virus (SEQ ID NO:4).

FIG. 8 is a slot blot of virus infected cells probed with adenovirus DNA (A) or human genomic DNA (loading control B).

FIG. 21 is that of EIB promoter (SEQ ID NO:7) changes as compared to Ad5 (SEQ ID NO:48) in a preferred construct or virus of the invention.

EXAMPLES

The inventors have constructed viruses with the aminoterminus of E1B 55K fused to GFP (comparative virus LGM), with replacement of the E2 promoter by three Tcf sites (virus Ad-Tcf3), and with the two combined (virus LGC). The inventors have also constructed viruses with replacement of the E2 promoter by four Tcf sites alone (virus vMB12), with replacement of the E2 promoter by four Tcf sites combined with silent mutations in the E3 promoter, particularly to NF1, NFκB, AP1, and ATF sites (virus vMB14), and with replacement of the E2 promoter by four Tcf sites combined with silent mutations in the E3 promoter, particularly to NF1, NFκB, AP1, but not ATF sites (virus vMB13). The inventors have also constructed viruses with replacement of the Sp1 site in the E1B promoter with four Tcf sites in a wild type adenovirus backbone (virus vMB23), in a vMB12 backbone (virus vMB27), in a vMB13 backbone (virus vMB31) and in a vMB14 backbone (virus vMB19).

Figure 4:
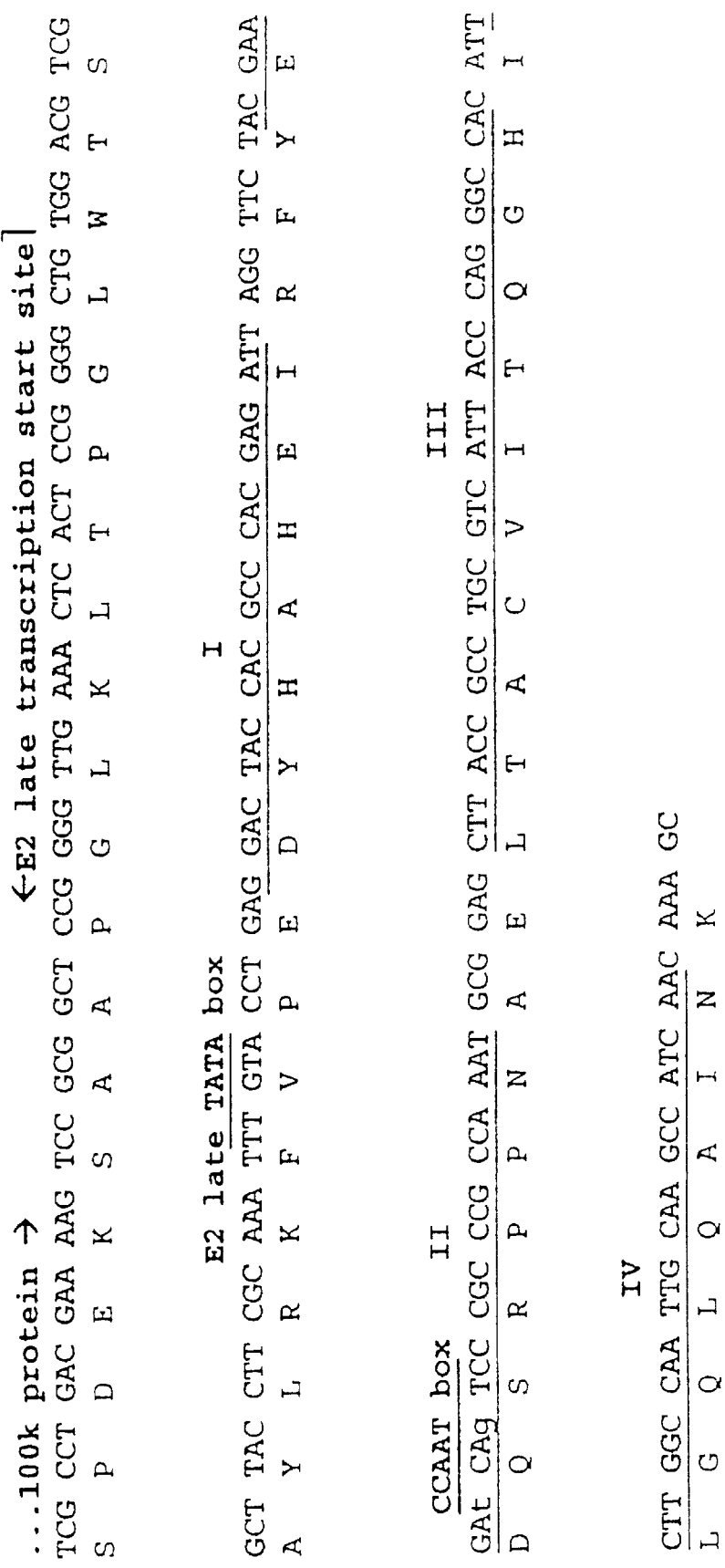
FIG. 4 shows E2 late promoter changes to wild type in a further preferred virus (SEQ ID NO:5).
Figure 5:
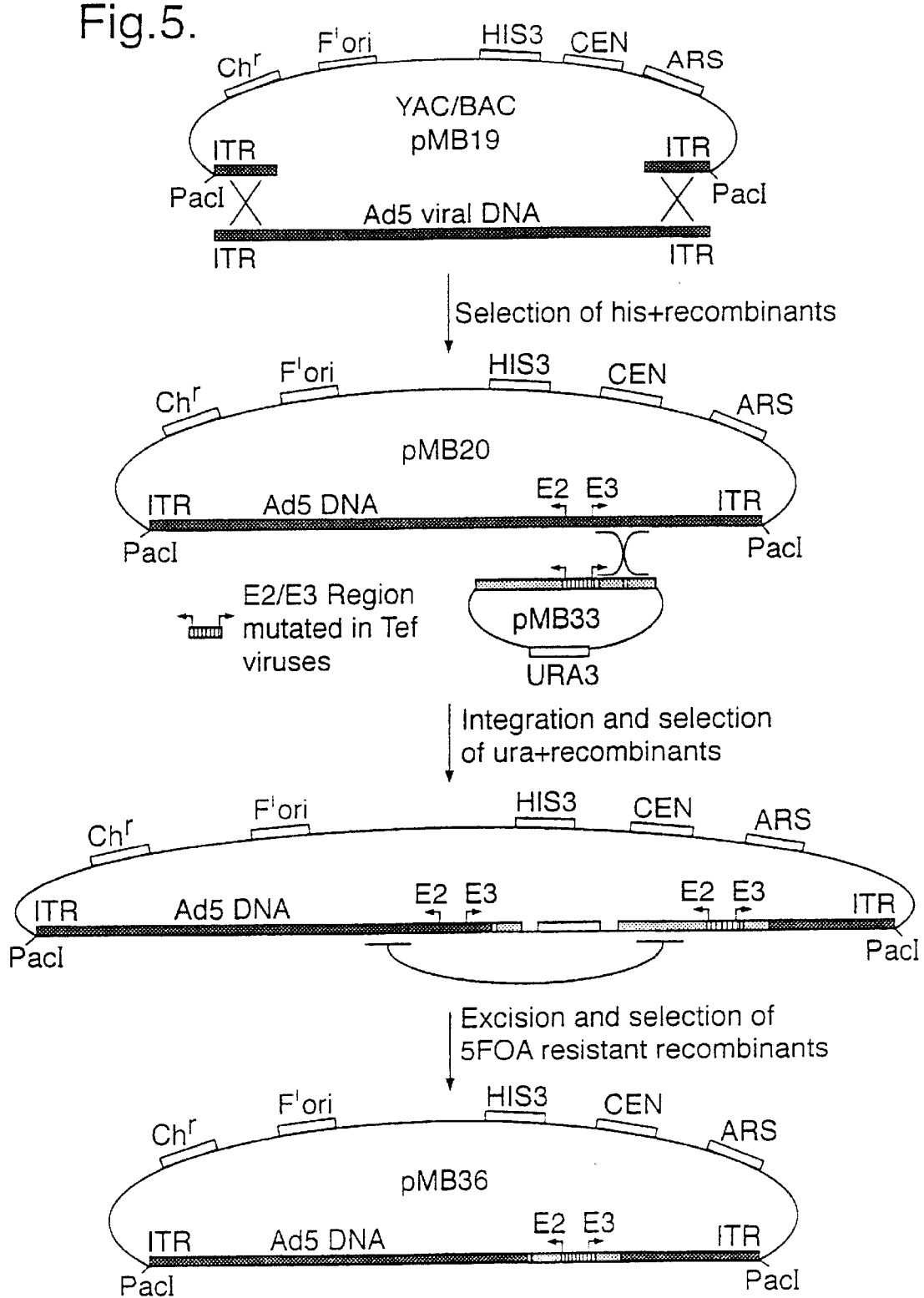
FIG. 5 shows a diagrammatic representation illustrating steps taken in production of viruses of the invention.
Figure 6:
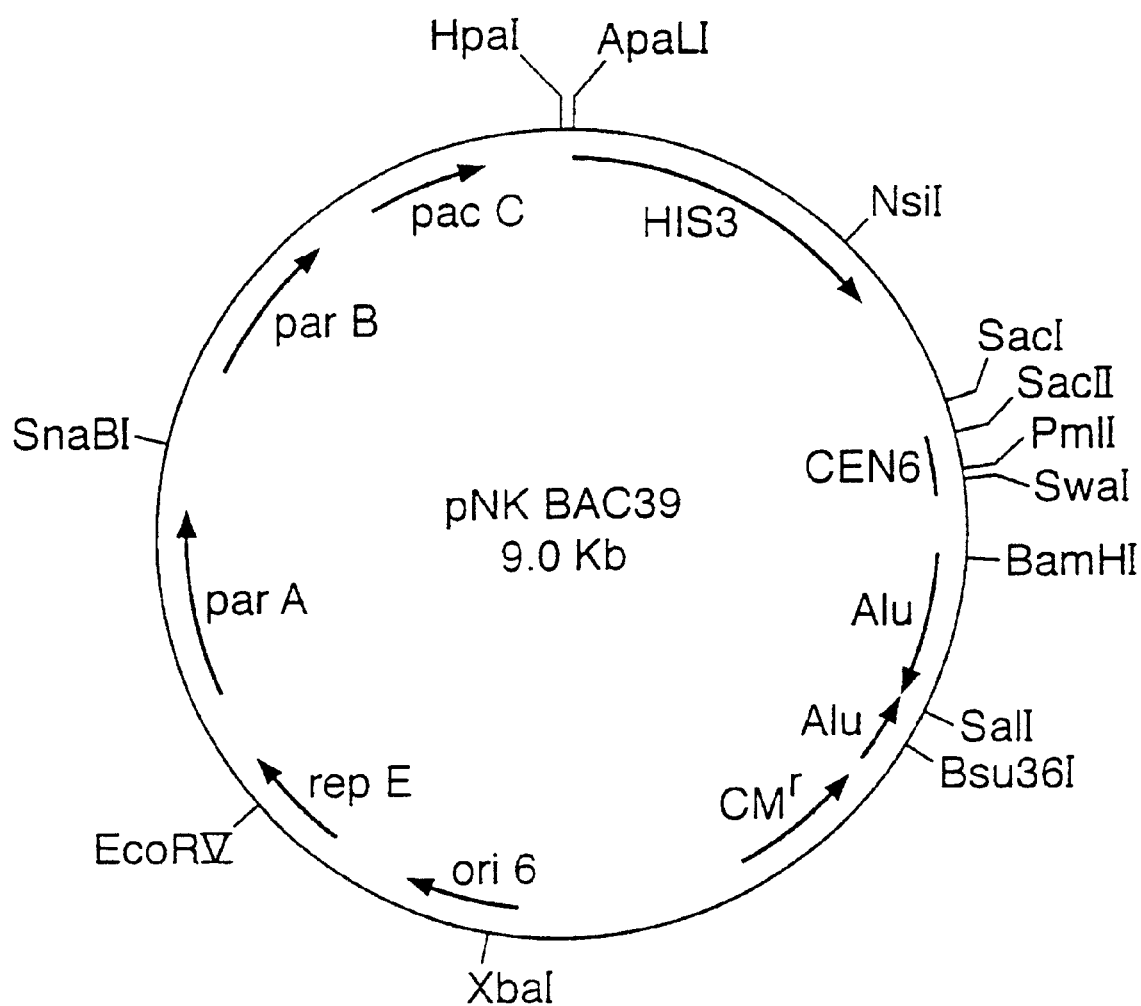
FIG. 6 is a diagrammatic representation of plasmid pNκBAC39.
Figure 7:
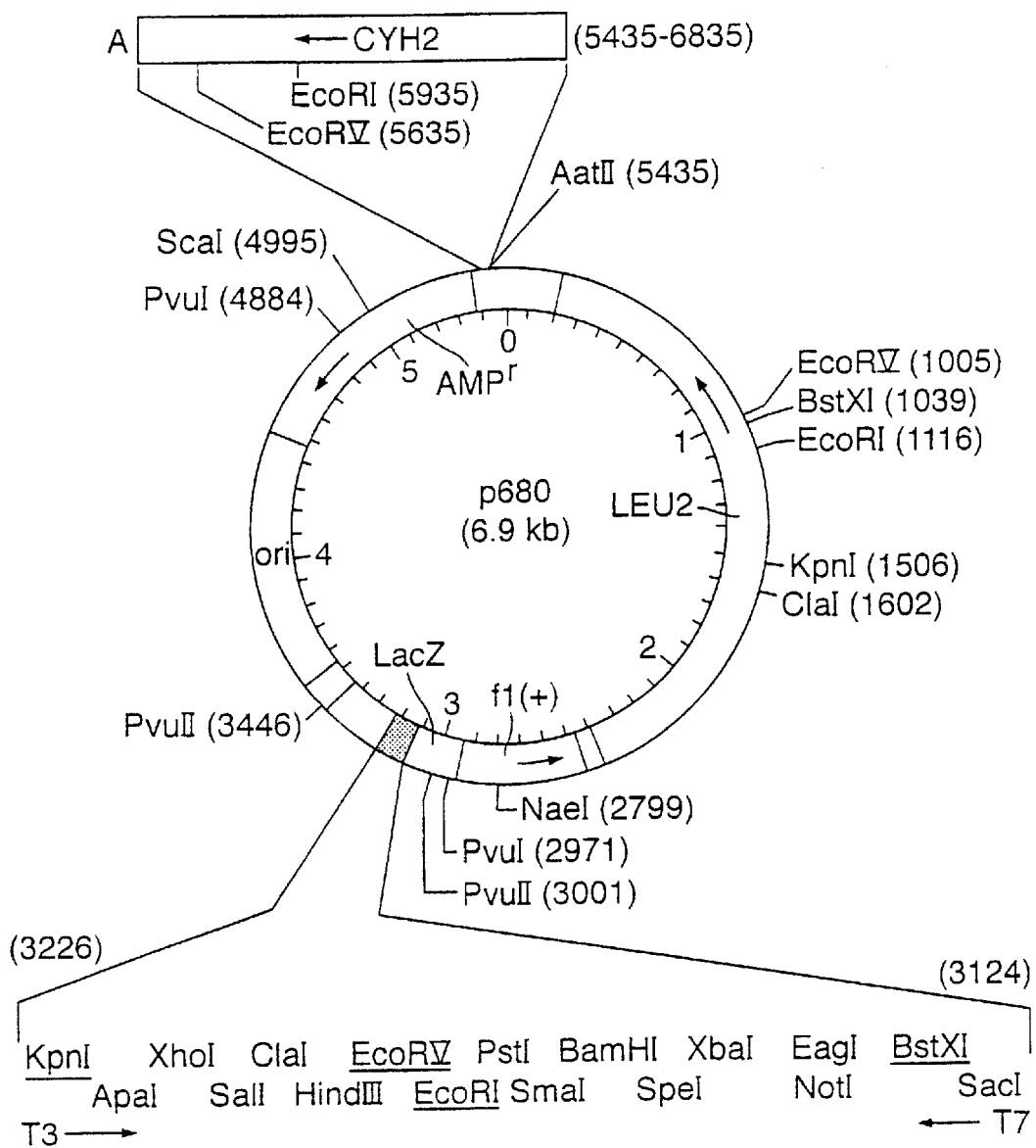
FIG. 7 is a diagrammatic representation of plasmid p680.

Brief Description of Key Constructs:

Gap repair and two step gene replacement as used to construct the Ad Tcf3 YAC/BAC (pMB36) are illustrated in FIG. 5 (all of the steps shown take place inside a yeast cell). Maps of pNKBAC39 and p680 are shown in FIGS. 6 and 7. Availability of materials: pUC19 (Clontech), Bluescript (Stratagene), pEGFP-C1 (Clontech), phGFP-S65T (Clontech) and pRS406 (Stratagene).

YAC/BAC (pMB19):

The adenovirus genome was modified in a large plasmid with a bacterial artificial chromosome (F') replication origin, a yeast centromere and replication origin, and selectable markers for yeast and bacteria (HIS3, chloramphenicol resistance gene).

Ad5 YAC/BAC (pMB20):

Genomic DNA was prepared from adenovirus type 5 obtained from ATCC (VR5). Small terminal fragments were amplified by PCR and cloned into the YAC/BAC. The vector was linearised at a site between the two terminal Ad5 fragments and transfected into yeast together with full length Ad5 genomic DNA. The plasmid was recircularised by homologous recombination (gap repair), giving full length Ad5 genomic DNA cloned in the YAC/BAC.

E1B::GFP fusion (pMB25): An Ad5 fragment containing the part of E1B 55k which overlaps E1B 19k was cloned by PCR and fused to the 5'-end of EGFP. This was then embedded in a larger Ad5 fragment, so that the E1B::GFP fusion was flanked on both sides by Ad5 sequence, in a vector containing LEU2 and CYH2 for selection and counter-selection in yeast.

LGM YAC/BAC (pMB26):

The E1B::GFP fusion in pMB25 was inserted in the Ad5 YAC/BAC by two step gene replacement. The resulting plasmid was transferred to E. coli to allow production of enough DNA for sequencing and transfection into mammalian cells. Plasmid from E. coli was cut with PacI to liberate the Ad 5 insert, then transfected into 293 cells to make virus.

E2-Tcfx3/4 Mutations (pMB33/69):

An Ad5 fragment containing the E2 region was cloned into a vector containing URA3 for selection and counterselection in yeast. The E2 promoter was replaced by inverse PCR. pMB33 contains 3 Tcf sites; pMB69 contains 4 Tcf sites.

Ad-Tcfx3 YAC/BAC (pMB36):

The E2-Tcfx3 replacement sequence in pMB33 was inserted in the Ad5 YAC/BAC by two step gene replacement. The YAC/BAC was then transferred to *E. coli* and 293 cells to make virus. The resulting virus is called Ad-Tcf3.

Ad-Tcfx4 YAC/BAC (pMB74):

The E2-Tcfx4 replacement sequence in pMB69 was inserted in the Ad5 YAC/BAC by two step gene replacement. The YAC/BAC was then transferred to *E. coli* and 293 cells to make virus. The resulting virus is called vMB12.

LGC YAC/BAC (pMB37):

The E2-Tcfx3 mutations in pMB33 were inserted in the LGM YAC/BAC by two step gene replacement. The YAC/BAC was then transferred to *E. coli* and 293 cells to make virus.

E2-Tcfx4/E3 Mutations (pMB66):

The E2 and E3 mutations were introduced in three successive rounds of inverse PCR. The E2 changes were made as for pMB33 but with four Tcf sites. To permit two step gene replacement some additional Ad 5 sequence was added 3' of the E3 promoter.

Ad-Tcfx4/mutE3 YAC/BAC (pMB75):

The E3 mutations and E2-Tcfx4 replacement sequence in pMB66 were inserted in the Ad5 YAC/BAC by two step gene replacement. The YAC/BAC was then transferred to *E. coli* and 293 cells to make virus. The resulting virus is called vMB14.

Ad-Tcfx4/mutE3+ATF YAC/BAC (pMB73):

The E3 mutations, except the ATF mutations, and E2-Tcfx4 replacement sequence in pMB66 were inserted in the Ad5 YAC/BAC by two step gene replacement. The YAC/BAC was then transferred to *E. coli* and 293 cells to make virus. The resulting virus is called vMB13.

Note: Both pMB73 and 75 were made by two step gene replacement in the Ad5 YAC/BAC using the pMB66. Mutations near the site of integration are not always transferred by two step gene replacement. pMB73 lacks the ATF site mutations because the ATF site is the nearest to the site of integration.

Detailed Procedures:

pMB20:

Ad5 genomic DNA was gap repaired into pMB19 cut with SalI. pMB19 was made by inserting a yeast replication origin (from pH4ARS, Bouton and Smith, 1986) into the SacI site of a vector already containing the terminal Ad5 fragments (pMB 10). The starting vector (pNKBAC39, Larionov et al., 1996) was expected not to need an ARS but this assumption proved incorrect. The Ad5 terminal fragments were cloned initially by PCR into a pUC19-derived vector (to give pMB1 and pMB2), and then transferred sequentially into the BamHI/Bsu36I sites of pNKBAC39. PacI sites were present in the G76 primer used to make pMB1 and pMB2 (PCR with primers G74-G76 and G75-G76 giving Ad5 fragments of 390 and 356 bp).

pMB25:

The EGFP vector is a modified vector from Clontech. It has the 5' end of GFP from pEGFP-C1 and the 3'-end of GFP from phGFP-S65T. The Ad5 PCR fragment (nt 2019–2261, primers G77–78) was cloned into the NheI and AgeI sites at the 5'-end of EGFP to give pMB7. The SmaI Ad5 fragment (nt 1007–3940) containing the E1 region was cloned into Bluescript to give pMB22. The E1B::GFP fusion (NotI/KpnI) was cloned into pMB22 (BglII/KpnI) to give pMB24. The XhoI/BamHI fragment of pMB24 containing the Ad5 insert was cloned into p680 (Ketner et al., 1994) to give pMB25.

pMB33:

The Ad5 PCR fragment (nt 26688–27593, PCR with primers G61-G62, product cut with SacI/KpnI) was cloned into the KpnI/SacI sites in pRS406 to give pMB32. This was mutagenised by inverse PCR to insert the Tcf sites using primers G63-G64. The primers should give four Tcf sites but the first Tcf site was subsequently found to contain a mutation, so the final vector only contains three Tcf sites.

pMB66:

pMB33 with four correct Tcf sites is called pMB69. pMB69 was mutagenised by inverse PCR using primers G89 and G90 to give pMB46. pMB46 was mutagenised by inverse PCR using primers G87 and G88 to give pMB49, which contains four Tcf sites in E2 and all of the desired mutations in E3. The Ad 5 PCR fragment (nt 27331–27689, primers G100-G101) used to facilitate two step gene replacement was cut with EcoRI and PstI and cloned into Bluescript to give pMB58. This 3' extension was first used to create a vector with four Tcf sites in E2 and a wild type E3 promoter (the EcoRI/PstI fragment from pMB58 was inserted into the EcoRI/SacI sites in pMB49) to give pMB63. The E3 mutations were then cloned back into this vector (the SacI/KpnI fragment of pMB49 was cloned into the SacI/KpnI sites in pMB63) to give pMB66.

pMB67:

The E2 promoter with two Tcf sites was constructed as for pMB33 but using primers G91 and G92 for the inverse PCR, to give pMB45. An EcoRI/Eco47III fragment containing the two Tcf sites was transferred from pMB45 into pMB66 to give pMB67.

```
Primers
G61   Ad 5,26688 (E2 region)                                    (SEQ ID NO:9)
5'-TGCATTGGTACCGTCATCTCTA-3'

G62   Ad 5, 27882 (E2 region)                                   (SEQ ID NO:10)
5'-GTTGCTCTGCCTCTCCACTT-3'

G63   iPCR, E2 promoter replacement (2 x Tcf), upper primer     (SEQ ID NO:11)
5'-CAGATCAAAGGGATTAAGATCAAAGGGCCATTATGAGCAAG-3'

G64   iPCR, E2 promoter replacement (2 x Tcf), lower primer     (SEQ ID NO:12)
5'-GATCCCTTTGATCTCCAACCCTTTGATCTAGTCCTTAAGAGTC-3'

G74   Ad5, 390 (left arm gap repair fragment)                   (SEQ ID NO:13)
5'-GGG GGA GTC TCC ACG TAA ACG-3'
```

-continued

```
G75   Ad5, 36581 (right arm gap repair fragment)                    (SEQ ID NO:14)
5'-GGG CAC CAG CTC AAT CAG TCA-3'

G76   Ad5 ITR plus EcoRI, HindiIII and PacI sites                   (SEQ ID NO:15)
5'-CGG AAT TCA AGC TTA ATT AAC ATC ATC AAT AAT ATA CC-3'

G77   Ad 5, 2020 (E1B fragment plus NheI site)                      (SEQ ID NO:16)
5'-GCG GCT AGC CAC CAT GGA GCG AAG AAA CCC A-3'

G78   Ad 5, 2261 (E1B fragment plus AgeI site)                      (SEQ ID NO:17)
5'-GCC ACC GGT ACA ACA TTC ATT-3'

G87   iPCR to destroy the E3 NF-1, Li and L2 binding sites, upper primer   (SEQ ID NO:18)
5'-AGCTGGGCTCTCTTGGTACACCAGTGCAGCGGGCCAACTA-3'

G88   iPCR to destroy the E3 NF-1, Li and L2 binding sites, lower primer   (SEQ ID NO:19)
5'-CCCACCACTGTAGTGCTGCCAAGAGACGCCCAGGCCGAAGTT-3'

G89   iPCR to destroy the E3 ATF and AP-1 binding sites, upper primer      (SEQ ID NO:20)
5'-CTGCGCCCCGCTATTGGTCATCTGAACTTCGGCCTG-3'

G90   iPCR to destroy the E3 ATF and AP-1 binding sites, lower primer      (SEQ ID NO:21)
5'-CTGCGGGCGGCTTTAGACACAGGGTGCGGTC-3 '

G91   iPCR, E2 promoter replacement (1 x Tcf), upper primer         (SEQ ID NO:22)
5'-CAGATCAAAGGGCCATTATGAGCAAG-3'

G92   iPCR, E2 promoter replacement (1 x Tcf), lower primer         (SEQ ID NO:23)
5'-GATCCCTTTGATCTAGTCCTTAAGAGTC-3'

G100  Ad 5, 27757 (E3 distal promoter region)                       (SEQ ID NO:24)
5'-ATGGCACAAACTCCTCAATAA-3'

G101  Ad 5, 27245 (E3 distal promoter region)                       (SEQ ID NO:25)
5'-CCAAGACTACTCAACCCGAATA-3'
```

The following references for procedures are incorporated herein by reference:

Bouton, A. H., and Smith, M. M. (1986). Fine-structure analysis of the DNA sequence requirements for autonomous replication of *Saccharomyces cerevisiae* plasmids. Mol Cell Biol 6, 2354–63.

Ketner, G., Spencer, F., Tugendreich, S., Connelly, C., and Hieter, P. (1994). Efficient manipulation of the human adenovirus genome as an infectious yeast artificial chromosome clone. Proc Natl Acad Sci U S A 91, 6186–90.

Larionov, V., Kouprina, N., Graves, J., Chen, X. N., Korenberg, J. R., and Resnick, M. A. (1996). Specific cloning of human DNA as yeast artificial chromosomes by transformation-associated recombination. Proc Natl Acad Sci U S A 93, 491–6.

E2 Promoter Replacement Sequences Inserts for Preparing Ad-Tcf Viruses

```
single Tcf site:                                    (SEQ ID NO:26)
AGATCAAAGGG Ad 5 sequence:                                      (SEQ ID NO:27)
GACTAG-....-GCCATT 2 Tcf sites:                                        (SEQ ID NO:28)
GACTAG-ATCAAAGGGATCCAGATCAAAGG-
GCCATT 3 Tcf sites:                                        (SEQ ID NO:29)
GACTAG-
ATCAAGGGTTGGAGATCAAAGGGATCCA-
GATCAAAGGGATTAA
GAT CAAAGG-GCCATT 4 Tcf sites:                                        (SEQ ID NO:30)
GACTAG-
ATCAAAGGGTTGGAGATCAAAGGGATC-
CAGATCAAAGGGATTA
AGATCAAAGG-GCCATT
```

Note: The 3 Tcf vector is a mutant form of the 4 Tcf vector resulting from a PCR cloning artefact (there is a single A deletion in the first Tcf site). This is the sequence present in the Ad-Tcf3 and LGC viruses.

E3 Promoter Binding Sites

Four sites have been identified in the E3 promoter by DNase I foot-printing in Hela cells (Garcia 1987, Hurst 1987) Site 1 covers the TATA box, the remaining sites (underlined and marked H2-H4 in FIGS. 1 to 3) are bound by ATF, AP1 and NF1. Two sites have been identified by DNase I footprinting in lymphoid cells (Williams 1990) (underlined and marked L1 and L2 in FIGS. 1 to 3), they bind NFκB family members.

To inactivate the promoter, mutations were introduced by inverse PCR. All sites except the TATA box contain at least one mutation. The mutations are silent at the protein level. The L1, L2 and H2 boxes contain multiple substitutions of highly conserved residues. The H4 box contains a single mutation in a relatively poorly conserved residue because of the limited choice of alternative codons. Mutation of the H4 site was not a priority because deletion of this site has no effect on E3 transcription in Hela cells (Garcia 1987). Only relatively weakly conserved residues in the H3 box were mutated because any modification of the most conserved residues in the published AP1 site (TGAC) would change the protein sequence. There is a better match to an AP1 site slightly 3' of the published site (still within the published footprint); the mutations introduced completely destroy this site.

Construction of Viruses Containing 4 Tcf Sites Controlling the E1B Promoter.

pMB22 (E1 region in Bluescript) is described in the construction of the LGM virus.

1. pRDI-238=Introduction of Tcf sites and deletion of Sp1 site by inverse PCR from pMB22. Primers: tCCCTTTGATCTccaaCCCTTTGATCT AGTCCtatataatgcgccgtg (SEQ ID NO:30) and tccAGAT-CAAAGGGattaAGATCAAAGGGatttaacacgccatgcaa (SEQ ID NO:31). The underlined sequence between the Tcf site and TATA box is identical with that in the E2 promoter (ie not E1B promoter sequence) because we know that this spacing and sequence are compatible with good regulation of the promoter.
2. pRDI-239=Transfer small fragment containing the Tcf mutations into a yeast integrating vector. The pRDI-238 EcoRI/SacI fragment was cloned into the same sites in pRS406.
3. pRDI-241=E1B-Tcf yeast integrating vector. The E1B-containing 2 kb SacI fragment from pMB22 was cloned into the same site in pRDI-239 to provide additional sequences for recombination with the YAC/BAC.
4. Two step gene replacement in YAC/BACs. pRDI-241 was cut with XbaI and transfected into yeast (yMB strains) containing the adeno YAC/BACs. To select for integration and excision, the transformants were plated on ura- then 5-FOA medium. Plasmids were then rescued to DH10B:

pRDI-243=recombinant from yMB2 (wild type Ad5)
    pRDI-268=recombinant from yMB15 (4xTcf-E2, wt E3)
    pRDI-254=recombinant from yMB13 (4xTcf-E2, mutant E3+wt ATF)
    pRDI-264=recombinant from yMB17 (4xTcf-E2, fully mutant E3)

5. These plasmids were cut with PacI and transfected into 293 cells (ATCC CRL 1573) containing activated Tcf (ΔNβ-catenin, supplied by Dr H Clevers) to produce recombinant adenoviruses:

vMB15=virus pool derived from pRDI-243 transfection
    vMB16=virus pool derived from pRDI-268 transfection
    vMB17=virus pool derived from pRDI-254 transfection
    vMB18=virus pool derived from pRDI-264 transfection 6. The viruses were plaque purified on SW480 cells because these cells contain active Tcf and have no endogenous E1B sequences with which the viral genome could recombine. The viruses were then expanded on SW480, purified by Cs banding, and checked by restriction digestion and sequencing in the E1B and E2/E3 regions. The plaque purified viruses were given the following names:

vMB23=Ad5 with 4 x Tcf sites in the E1B promoter
    vMB27=Ad5 with 4 x Tcf sites in both the E1B and E2 promoters
    vMB31=Ad5 with 4 x Tcf sites in the E1B and E2 promoters, and a mutant E3 promoter with a wild type ATF site
    vMB19=Ad5 with 4 x Tcf sites in the E1B and E2 promoters, and a fully mutant E3 promoter Results:

Luciferase assays using Tcf reporters show that p53-mutant lung carcinoma cells (H1299) lack Tcf activity and p53-mutant colon carcinoma cells (SW480) have strong Tcf activity. Viruses selective for cells containing Tcf activity should therefore replicate in SW480 but not H1299. The inventors have demonstrated that matched viruses with Tcf-mutant E2 promoters express E2 gene products preferentially by western blotting; replicate better by slot blotting and quantitative PCR; and have greater cytopathic effect in SW480 than H1299. The relatively modest effect of an E2 promoter mutation alone is considerably enhanced when the virus also lacks E1B 55k. E1B 55k mutations reduce nuclear export of DBP mRNA transcribed from the E2 late promoter. DBP can be expressed from both the early and late E2 promoters. The inventors have determined that the E1B 55k-dependent reduction in DBP expression might be rescued by the Tcf mutations in the E2 early promoter. Consistent with this the level of DBP expressed from LGC is significantly reduced in H1299. This effect of E1B 55k is entirely independent of p53, as is obvious from the fact that neither cell line contains p53.

Western Blot

H1299 and SW480 were infected at an moi of 0.2 with wild type Ad5, Ad-Tcf3, LGM and LGC. Cells were harvested for western blotting after 24, 48 and 72 hours. Blots were probed with antibodies against DBP. Wild type Ad5 gave comparable expression of protein in SW480 and H1299. Ad-Tcf3 gave slightly stronger expression of DBP in SW480 than in H1299. Ad-Tcf3 gave higher expression of DBP protein than wild type Ad5 in SW480 at 24 hours, but was similar to wild type Ad5 at 48 and 72 hours. DBP was expressed better by LGM than LGC in H1299, but both viruses gave comparable DBP expression in SW480.

The results are consistent with the Tcf-mutant E2 promoter being more strongly activated in colon cells than in lung cells.

Viral DNA Replication Assays

Figure 9:
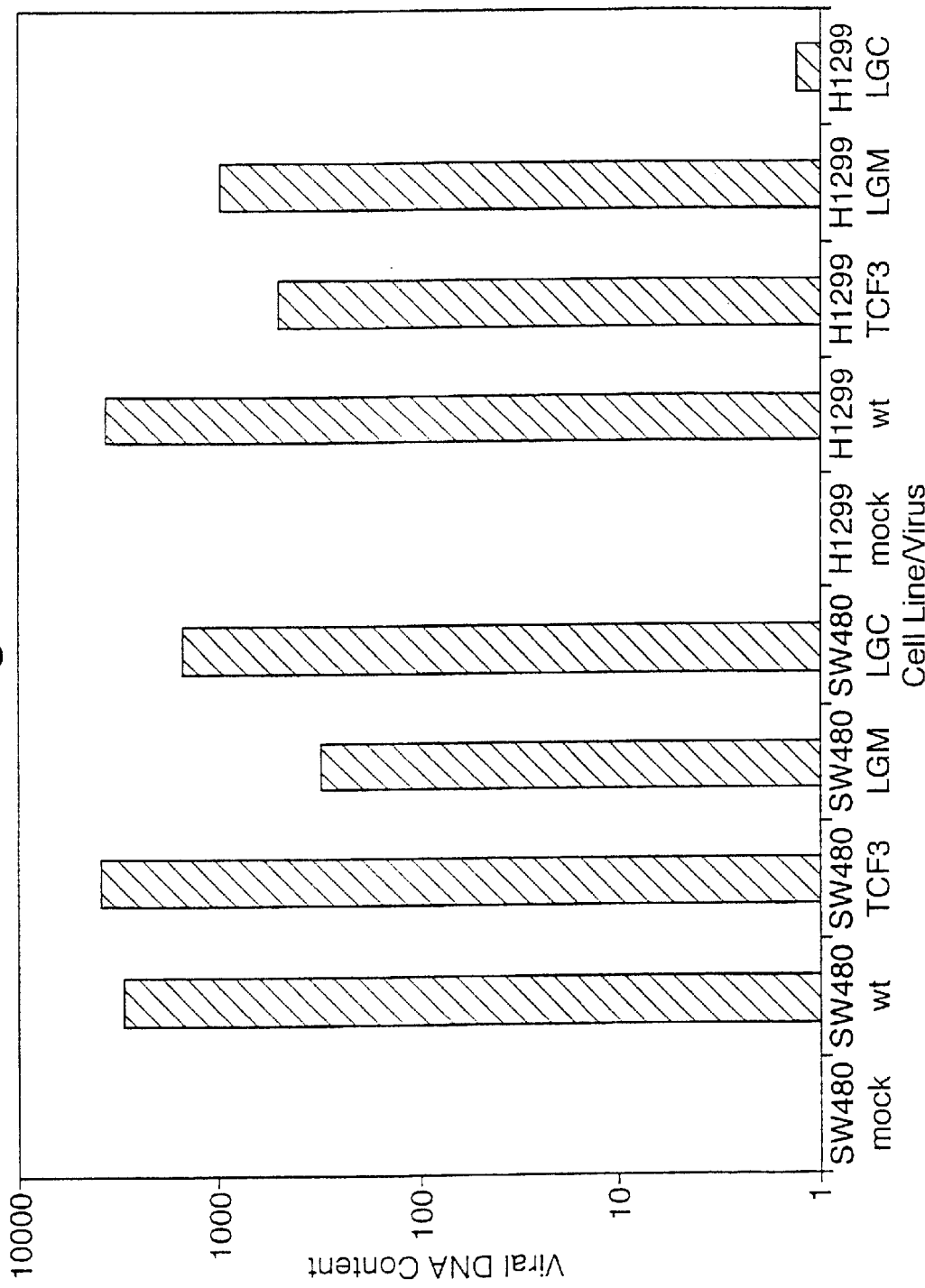
FIG. 9 is a graphic representation of results of quantatative PCR of viral DNA from virus infected cells.

H1299 and SW480 were infected at an moi of 0.2 with wild type Ad5, Ad-Tcf3, LGM and LGC. Cells were harvested for DNA extraction after 0, 24, 48 and 72 hours. All of the samples were slot blotted and hybridised to $^{32}$P-labelled adenoviral DNA (FIG. 8A) or control human genomic DNA (FIG. 8B). This showed replication of LGM in both cell lines, but replication of LGC only in SW480 (the actual values measured by phosphorimager are equal to background). To calculate the difference more precisely, the 72 hour samples were tested by Taqman quantitative PCR assay (Perkin Elmer) using Ad5 primers (FIG. 9). This confirmed the results of the slot blot: LGC is two-fold worse than wild type Ad5 in SW480, but 3000-fold worse in H1299. LGM is ten-fold worse than wild type Ad5 in SW480, but four-fold worse in H1299. Ad-Tcf3 also shows some selectivity for SW480 cells, albeit less dramatic: it is 1.3-fold better than wild type Ad5 in SW480, but 7.4-fold worse in H1299.

These results are consistent with the stronger expression of pol and pTP in Tcf-mutant E2 promoter viruses in colon cells resulting in greater viral replication. Additionally, the data show that the combination of an E2 promoter mutation with deletion of E1B 55k results in exceptionally little replication in cells lacking Tcf activity.

Cytopathic Effect (CPE) Assays

H1299 and SW480 were infected with five-fold dilutions of wild type AdS, Ad-Tcf3, LGM and LGC (moi of 0.6 in well 1, moi of 0.001 in well 5). Dishes were stained with crystal violet after eight days. CPE is apparent with wild type Ad5 in H1299 even at the highest dilution. Wild type Ad5 is five-fold less active in SW480 than H1299.

Ad-Tcf3 is five-fold less active than wild type Ad5 in H1299. LGM is 125-fold less active than wild type Ad5 in H1299. LGC is 625-fold less active than wild type AdS in H1299. The Tcf3 mutation in the E2 promoter thus results in a five-fold reduction in CPE in H1299. Ad-Tcf3 is similar to wild type Ad5 in SW480, indicating that there is a five-fold gain in activity in cells containing Tcf activity. LGC is five-fold more active than LGM in SW480.

LGC is 625-fold less active than wild type Ad5 in cells lacking Tcf activity, but only five-fold less active in cells containing Tcf activity. This represents a 125-fold selectivity for colon cells, and a five-fold greater activity than a simple E1B 55k-deficient virus.

Additional CPE assays were performed with SW480 cells and normal lung fibroblasts using the above viruses Ad-Tcf3, LGM and LGC. Ad-Tcf3 gave wild type activity on SW480 but 5-fold less activity on normal fibroblasts. In this experiment LGM and LGC both gave about 125-fold less activity than wild type Ad5 on SW480 but 5-fold and >125-fold less activity respectively on normal fibroblasts.

The selectivity and efficacy of Ad-Tcf 3 are shown to be greater than that of LGM which itself has essentially the same properties as the ONYX-015 virus.

4xTcf Viruses vMB12, 13, 14 and 19

Methods:

Cell lines: SW480 and Co115 colorectal carcinoma cells were supplied by Dr B Sordat. WI38 cells were supplied by ATCC. The H1299 cells were supplied by Dr C Prives and contain an integrated tet-VP16 transactivator (Chen, X., et al. 1996. Genes Dev 10, 2438–51).

Taqman Assays

Cells were infected with either 300 (SW480 and H1299) or 1000 (WI38) viral particles/cell in DMEM 10% FCS. Two hours after infection, the medium was removed and replaced with 2 ml of fresh DMEM 10% FCS containing 10 mM hydroxyurea. Twenty-four hours after infection, cells are washed with 1× PBS and lysed with either buffer RLT (from Qiagen RNeasy Mini Kit, Ref. 74104) for RNA extraction or with a mix containing 1× PBS, buffer AL and proteinase K solution (from Qiagen DNeasy Tissue Kit, Ref. 69504) for DNA extraction. RNA and DNA extractions were performed according to the manufacturer's instructions. Reverse transcription (RT) was performed using 1 μg of total RNA and MMLV Superscript Core Reagents (LifeTechnologies, Ref. 18064022) in 20 μl reaction volume. TaqMan PCR reactions were performed using TaqMan Universal PCR Master Mix Kit (Perkin Elmer, Ref. 4304447), 900 nM of primers (Microsynth and Eurogentec) and 500 nM of TaqMan probe (Eurogentec). Sybr green PCR reactions were performed using Sybr green Universal PCR Master Mix Kit (Perkin Elmer, Ref. 4309155) and 900 nM of fibre gene primers (Eurogentec). The amount of template used for the PCR reaction was 1 μg of genomic DNA or to 5 μl of RT reaction volume. Results for DNA were normalised to $OD_{260}$, results for RNA were normalised to ribosomal RNA (Ribosomal RNA Control, Perkin Elmer, ref 4310893E). The primers and probes for quantitative PCR were

| | | |
|---|---|---|
| E2 early forward primer: | TTCGCTTTTGTGATACAGGCA | (SEQ ID NO:32) |
| E2 early reverse primer: | GTCTTGGACGCGACGAGAAG | (SEQ ID NO:33) |
| E2 probe: | CGGAGCGTTTGCCGCGC | (SEQ ID NO:34) |
| E3 forward primer: | AGCTCGGAGAGGTTCTCTCGTAG | (SEQ ID NO:35) |
| E3 reverse primer: | AACACCTGGTCCACTGTCGC | (SEQ ID NO:36) |
| E3 probe: | CCGCGACTCCGTTTCAACCCAGA | (SEQ ID NO:37) |
| E1B-55k forward primer: | TGCTTCCATCAAACGAGTTGG | (SEQ ID NO:38) |
| E1B-55k reverse primer: | GCGCTGAGTTTGGCTCTAGC | (SEQ ID NO:39) |
| E1 B-55k probe: | CGGCGGCTGCTCAATCTGTATCTTCA | (SEQ ID NO:40) |
| E4 forward primer: | GGTTGATTCATCGGTCAGTGC | (SEQ ID NO:41) |
| E4 reverse primer: | ACGCCTGCGGGTATGTATTC | (SEQ ID NO:42) |
| E4 probe: | AAAAGCGACCGAAATAGCCCG | (SEQ ID NO:43) |
| Fibre forward primer: | TGATGTTTGACGCTACAGCCATA | (SEQ ID NO:44) |
| Fibre reverse primer: | GGGATTTGTGTTTGGTGCATTAG | (SEQ ID NO:45) |

Western Blot Analysis

Cells were infected with either 300 (SW480 and H1299) or 1000 (WI38) viral particles/cell in DMEM 10% FCS. Two hours after infection, the medium was removed and replaced with 2 ml of fresh DMEM 10% FCS. Cells were harvested 24 hours after infection. Immunoblotting was performed as described by Harlow and Lane (Antibodies: A laboratory manual, New York: Cold Spring Harbor Laboratory Press, 1988 incorporated herein by reference). Dr. A. Levine provided both 2A6 anti-E1B55K antibody (Sarnow P. et al, Virology, 1982, 120: 510–517) and B6 anti-DBP antibody (Reich N. et al, Virology, 1983, 128: 480–484). Detection was with HRP-conjugated rabbit anti-mouse IgG (DAKO A/S, Denmark) and chemiluminescence (Amersham, Little Chalfont, UK).

Plaque Assay

Cells were infected in duplicate with either 300 (for SW480 and H1299) or 1000 (WI38) viral particles/cell in DMEM 10% FCS. After two hours incubation at 37° C., the medium was removed and replaced with 2 ml of fresh DMEM 10% FCS. After an additional 48 hours, the cells were scraped into the culture medium and lysed by three cycles of freeze-thawing. The supernatant of each duplicate point was tested for virus production by triplicate plaque assay for 8–10 days under semisolid agarose on SW480 cells Cytopathic Effect Assays For the cytopathic effect assays, SW480 and H1299 cells were plated in triplicate in 96-well plates and infected with five-fold dilutions of virus from 1000 to 0.06 viral particles/cell. After two hours incubation at 37° C., an additional 100 μl of DMEM 10% FCS was added to each well. After six days, the assays was terminated and the protein content in each well was measured using the BCA Protein Assay Kit (Pierce, Rockford, Ill., USA) according to the manufacturer's instructions.

Xenografts

One million Co115 cells were injected subcutaneously into the flank of nude mice. On days 4–8 after injection, $3\times10^{10}$ particles of virus or buffer were injected directly into the tumour. Tumour size was measured in two dimensions with callipers and tumour volume was calculated using the formula: volume=0.4×length×width$^2$.

Cotton Rat Lungs

Cotton rats were infected intranasally with $3\times10^{10}$ particles of virus in 50 µl of buffer. Three days later the animals were killed with isoflurane and four fragments of lung (from left and right upper and lower lobes) were taken from each animal. DNA was extracted by Qiagen DNeasy Tissue Kit and the samples from each animal pooled. Viral DNA content was determined by Taqman PCR with E4 primers and probe using 100 ng input DNA, as described above.

Results: vMB12, 13, 14 and 19

Figure 10:
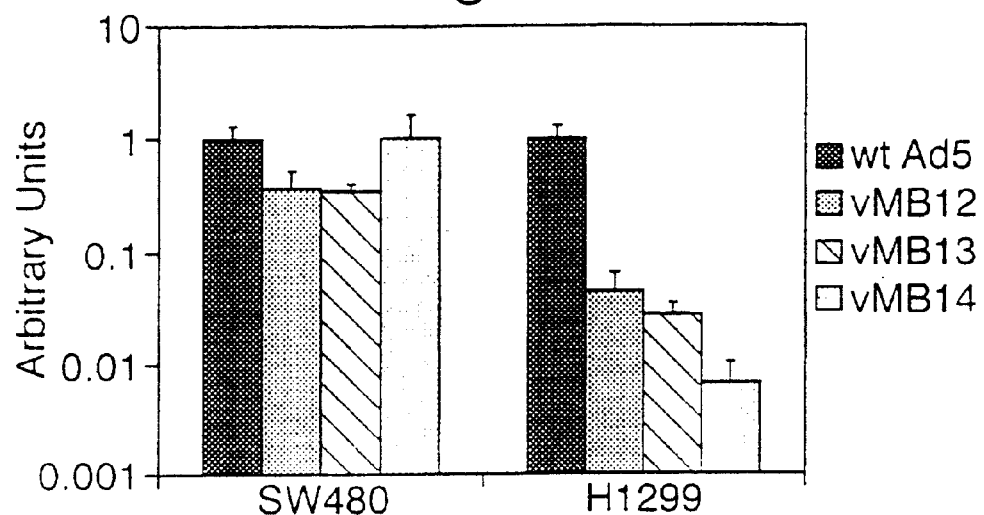
FIG. 10 is a histogram showing E2 early expression in SW 480 and H1299 cell lines infected with wild type Ad5, and vMB12, vMB13 and vMB14 of the invention as measured by Taqman RT-PCR.
Figure 11:
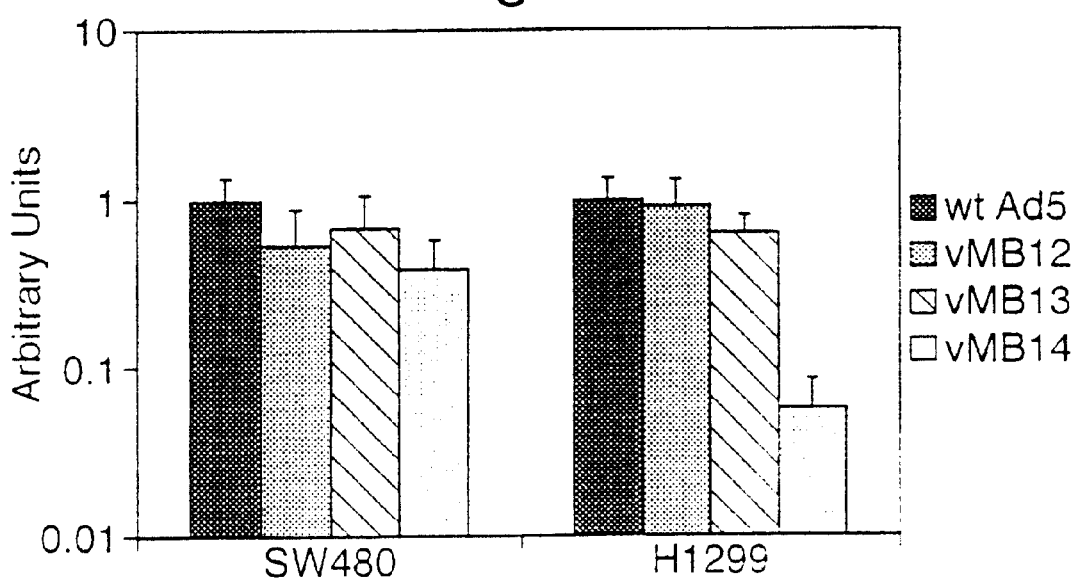
FIG. 11 is a histogram showing E3 expression in SW480 and H1299 cell lines infected with wild type Ad5, and vMB12, vMB13 and vMB14 of the invention as measured by Taqman RT-PCR.
Figure 12:
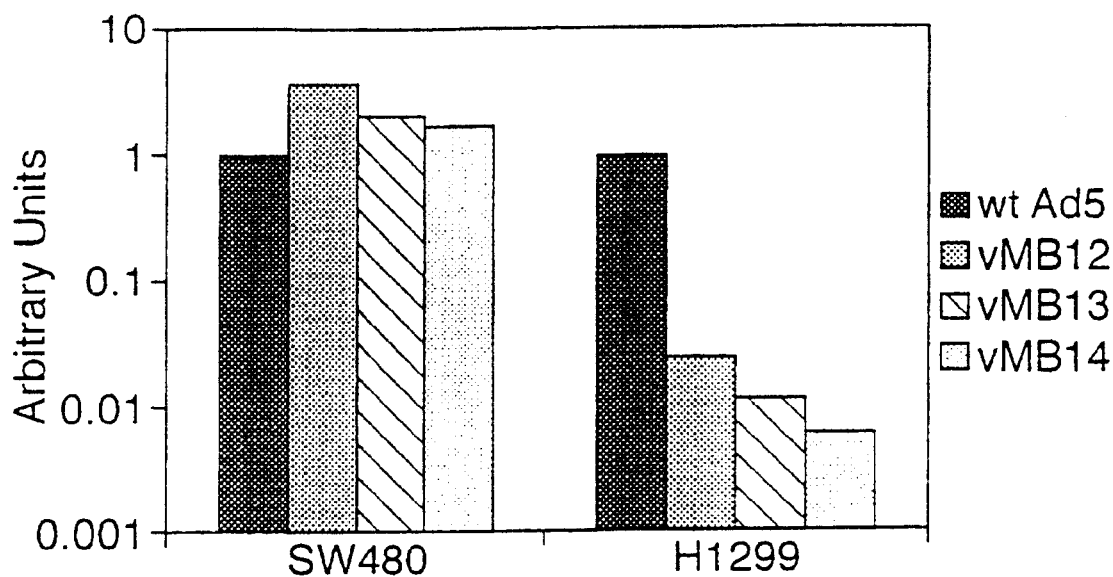
FIG. 12 is a histogram showing DNA replication of wild type Ad5, and vMB12, vMB13 and vMB14 of the invention in SW480 and H1299 cell lines as measured by Taqman RT-PCR.
Figure 13:
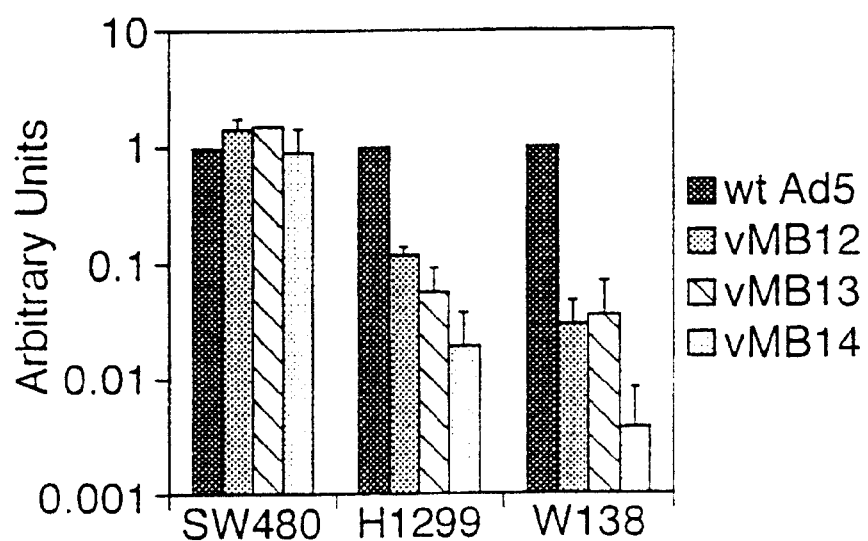
FIG. 13 is a histogram showing burst size (arbitrary units) with wild type Ad5, and vMB12, vMB13 and vMB14 of the invention in SW480, H1299 and W138 (fibroblast) cell lines.
Figure 14:
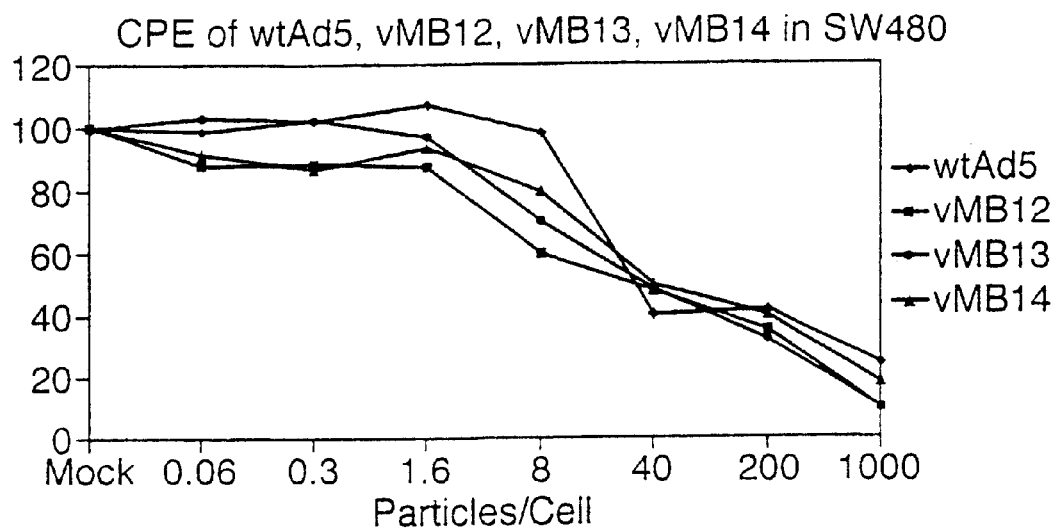
FIG. 14 is a graph showing CPE results % v particles/cell of wild type Ad5, and vMB12, vMB13 and vMB14 of the invention in SW480
Figure 15:
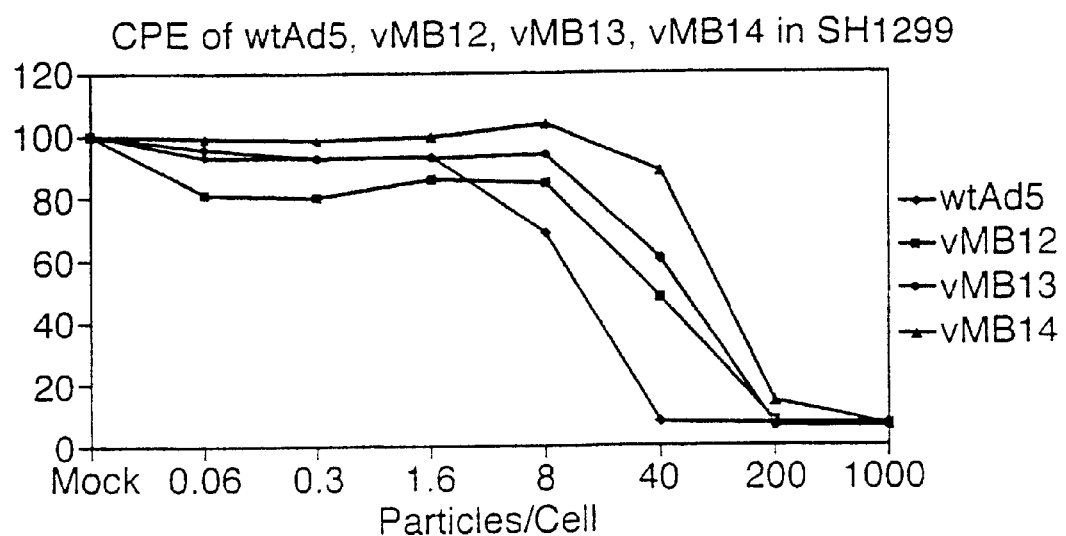
FIG. 15 is a graph showing CPE results % v particles/cell of wild type Ad5, and vMB12, vMB13 and vMB14 of the invention in H1299.
Figure 16:
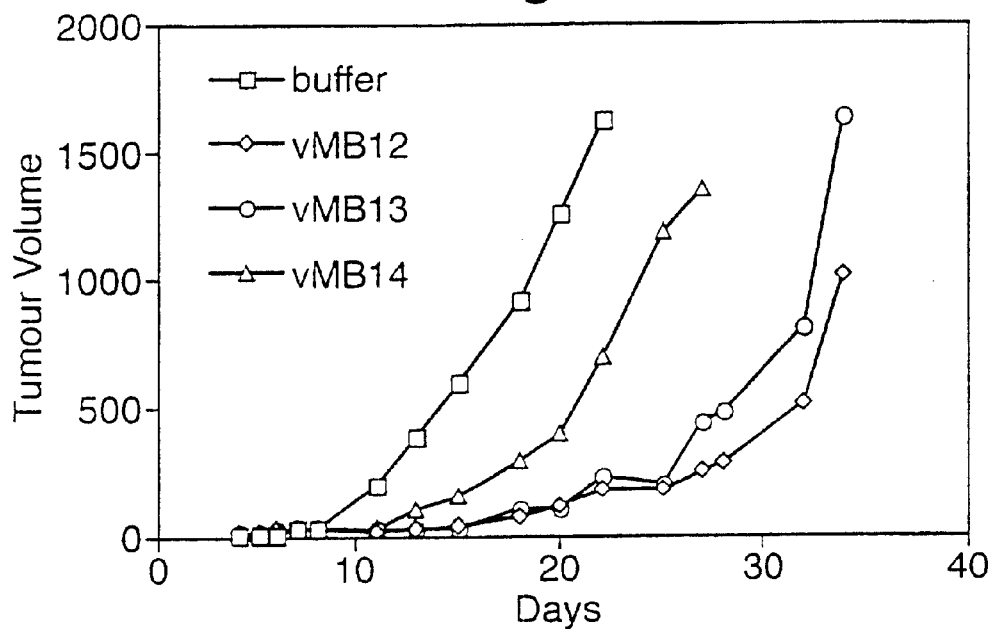
FIG. 16 is a plot of tumour volume v days after administration of buffer, vMB12, vMB13 and vMB14 in Co115 xenografts.
Figure 17:
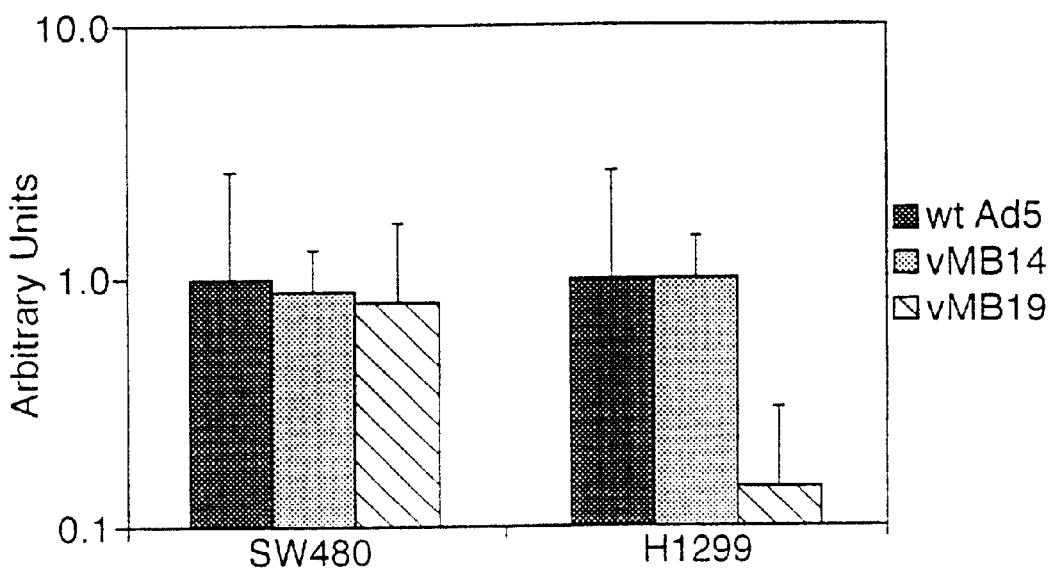
FIG. 17 is a histogram showing E1B-55k expression in SW480 and H1299 cell lines infected with wt Ad5, vMB14 and vMB19 of the invention.
Figure 18:
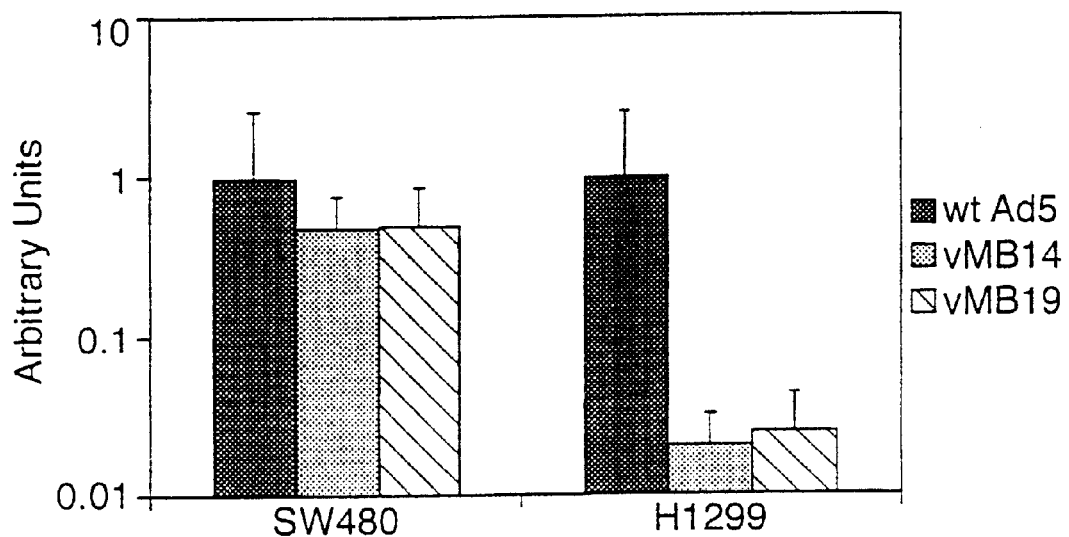
FIGS. 18, 19 and 20 are histograms of E2 and E3 early expression and DNA replication respectively in SW480 and H1299 cells.
Figure 19:
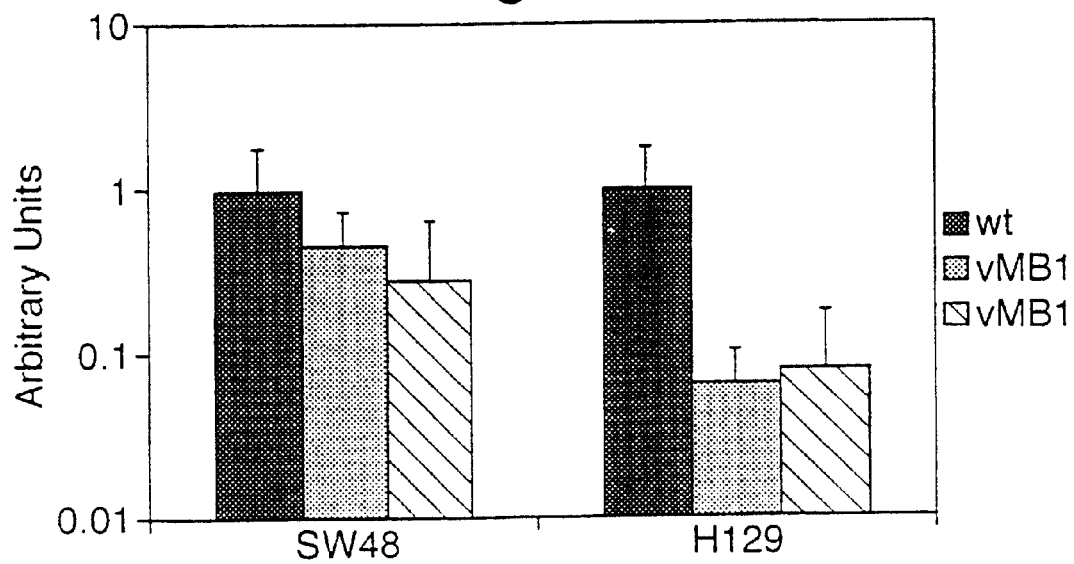
Figure 20:
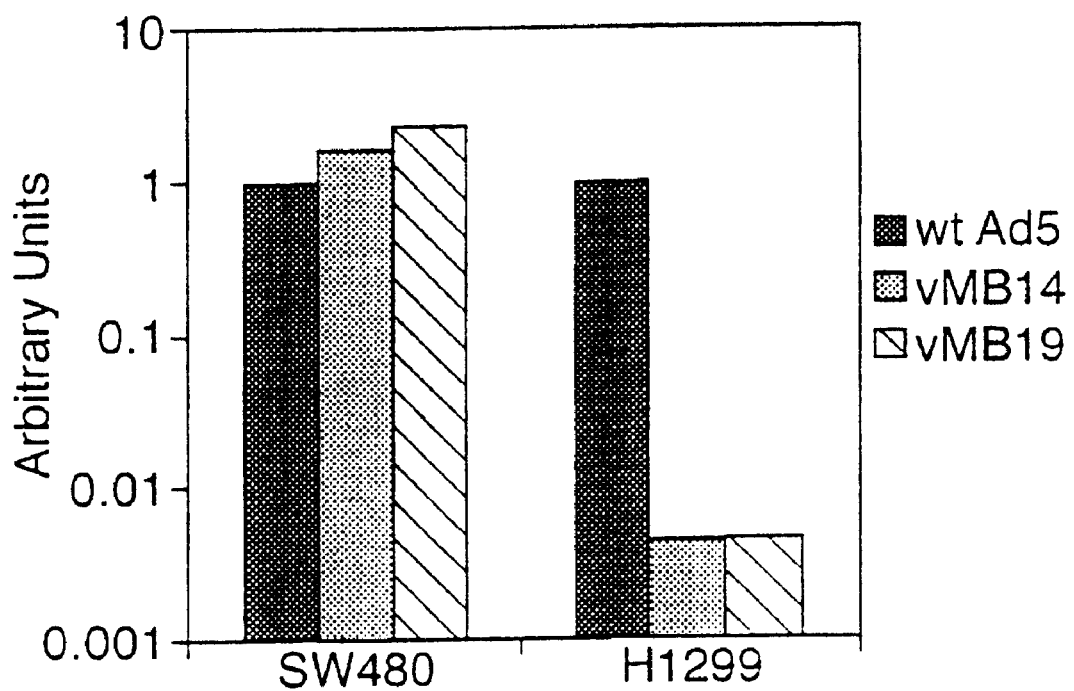

The viruses with four Tcf sites in the E2 promoter were tested in SW480, H1299 and W138 cells. Cells were harvested 24 hours after infection. Western blotting for DBP showed that DBP is expressed at least as well by the mutant viruses as by wild type in SW480, but much worse in H1299 and W138 cells:

Taqman RT-PCR transcription assays (see FIG. 10) show mutant viruses to have wild type levels of E2 mRNA in SW480 cells, but reduced levels in H1299 cells:

The Taqman assay further demonstrates that mutation of the E3 promoter in vMB14 decreases both E2 (FIG. 10) and E3 mRNA levels (FIG. 11):

To determine whether DNA replication is affected by the promoter mutations, SW480 and H1299 cells were infected with wild type, vMB12, 13 and 14, and harvested at 24 hours. Sybr green PCR assays using primers from the fibre region show that DNA replication is normal in SW480 but reduced in H1299 cells (FIG. 12):

To determine whether virus replication is affected by the promoter mutations, SW480 and H1299 cells were infected with wild type, vMB12, 13 and 14, and harvested at 48 hours. Cells were lysed by freeze-thawing and virus production was measured by plaque forming assay on SW480 cells. This showed that the mutant viruses are comparable or better than wild type in SW480 cells, but defective in H1299 and W138 cells (See FIG. 13):

To determine whether the viruses show selective toxicity to colon cells, cytopathic effect assays were performed on SW480 and H1299 cells. This showed that the mutant viruses are comparable to wild type in SW480 cells (FIG. 14) but showed reduced cytopathic effect in H1299 cells (FIG. 15):

To determine whether the viruses show a therapeutic effect in vivo, they were injected into Co115 colon carcinoma xenografts in nude mice. This showed that intratumoral injection of all of the viruses delay the growth of xenografted colon tumours and prolong the survival of nude mice. vMB12 and 13 were more effective than vMB14 (FIG. 16):

E1B expression is required for induction of inflammatory damage by adenoviruses in cotton rat lung (Ginsberg, H. S., et al 1999. PNAS 96, 10409–11). To reduce the risk of inflammatory reactions, Tcf sites were cloned into the E1B promoter. The resulting viruses should express E1B gene products in colon tumour cells but not in normal cells. In addition to reducing the risk of inflammatory reactions, this could also reduce expression of E2 gene products from the E2 late mRNA, because E1B 55k is reported to be required for E2 late mRNA export. The virus with the mutant E1B promoter cloned into the vMB14 backbone is called vMB19. Wild type, vMB14 and vMB19 were tested in SW480 and H1299 cells. Cells were harvested 24 hours after infection. Western blotting for E1B and DBP showed that E1B 55k is expressed in SW480 but not in H1299. vMB14 and 19 gave similar DBP expression in H1299 cells, suggesting that there is not a large effect of E1B on DBP late mRNA export, at least at 24 hours in this cell line:

Taqman RT-PCR transcription assays 24 hours after infection confirmed that the vMB19 has wild type levels of E1B, E2 and E3 mRNA in SW480 cells, but reduced levels in H1299 cells (FIGS. 17, 18 and 19):

Viral DNA replication was tested 24 hours after infection by Sybr green quantitative PCR using fibre primers. This showed that both mutant viruses replicate normally in SW480 cells but are defective in H1299 cells. Both mutant viruses were comparable, again suggesting that the documented reduction in E1B 55k expression does not have a marked effect in this experiment (FIG. 20):

To determine whether vMB19 shows reduced DNA replication in normal cells in an in vivo setting, cotton rats were infected intra-nasally with virus and DNA was extracted from lungs three days later. Rats were treated in groups of five for each virus. Taqman quantitative PCR using E4 primers showed a median 50-fold reduction in viral DNA concentration with vMB19 compared to wild type.

Conclusions: vMB12, 13, 14 and 19

These data show that 1. insertion of Tcf sites in the E2 promoter is compatible with the production of viable adenovirus
2. the mutant E2 promoter is more active in colon tumour cells than non-colon tumour cells
3. mutation of the E3 promoter further reduces E2 activity in non-colon tumour cells
4. these mutations reduce viral DNA replication, virus replication and cytopathic effect in non-colon tumour cells
5. the mutant viruses impair the growth of xenografts in nude mice
6. insertion of Tcf sites in the E1B promoter is compatible with the production of viable adenovirus
7. the mutant E1B promoter is more active in colon tumour cells than non-colon tumour cells
8. in the models tested so far the E1B promoter mutation does not affect virus replication
9. the virus with combined E1B and E2/E3 promoter mutations shows reduced replication in cotton rat lungs, and is expected to produce less inflammatory damage than viruses with the E2/E3 mutations alone.

REFERENCES

Bartek, J., Bartkova, J., and Lukas, J. (1997). The retinoblastoma protein pathway in cell cycle control and cancer. Exp Cell Res 237, 1–6.

Bischoff, J. R., Kim, D. H., Williams, A., Heise, C., Horn, S., Muna, M., Ng, L., Nye, J. A., Sampson-Johannes, A., Fattaey, A., and McCormick, F. (1996). An adenovirus mutant that replicates selectively in p53-deficient human tumor cells. Science 274, 373–6.

Meta-Analysis Group in Cancer, (1996). Reappraisal of hepatic arterial infusion in the treatment of nonresectable liver metastases from colorectal cancer. J Natl Cancer Inst 88, 252–8.

Chartier, C., Degryse, E., Gantzer, M., Dieterle, A., Pavirani, A., and Mehtali, M. (1996). Efficient generation of recombinant adenovirus vectors by homologous recombination in *Escherichia coli*. J Virol 70, 4805–10.

Clayman, G. L., el-Naggar, A. K., Lippman, S. M., Henderson, Y. C., Frederick, M., Merritt, J. A., Zumstein, L. A., Timmons, T. M., Liu, T. J., Ginsberg, L., Roth, J. A., Hong, W. K., Bruso, P., and Goepfert, H. (1998). Adenovirus-mediated p53 gene transfer in patients with advanced recurrent head and neck squamous cell carcinoma. J Clin Oncol 16, 2221–32.

Croyle, M. A., Stone, M., Amidon, G. L., and Roessler, B. J. (1998). In vitro and in vivo assessment of adenovirus 41 as a vector for gene delivery to the intestine. Gene Ther 5, 645–654.

Crystal, R. G., Hirschowitz, E., Lieberman, M., Daly, J., Kazam, E., Henschke, C., Yankelevitz, D., Kemeny, N., Silverstein, R., Ohwada, A., Russi, T., Mastrangeli, A., Sanders, A., Cooke, J., and Harvey, B. G. (1997). Phase I study of direct administration of a replication deficient adenovirus vector containing the *E. coli* cytosine deaminase gene to metastatic colon carcinoma of the liver in association with the oral administration of the pro-drug 5-fluorocytosine. Hum Gene Ther 8, 985–1001.

Cunningham, D., Pyrhönen, S., James, R. D., Punt, C. J. A., Hickish, T. S., Heikkila, R., Johannesen, T., Starkhammar, H., Topham, C. A., Ong, E., Herait, P., and Jacques, C. (1998). A phase III multicenter randomized study of CPT-11 versus supportive care alone in patients with 5FU-resistant metastatic colorectal cancer. Proc Am Soc Clin Oncol 17, abstract 1.

Dahmane, N., Lee, J., Robins, P., Heller, P., and Ruiz i Altaba, A. (1997). Activation of the transcription factor Gli1 and the Sonic hedgehog signalling pathway in skin tumours. Nature 389, 876–81.

Ellisen, L. W., Bird, J., West, D. C., Soreng, A. L., Reynolds, T. C., Smith, S. D., and Sklar, J. (1991). TAN-1, the human homolog of the Drosophila notch gene, is broken by chromosomal translocations in T lymphoblastic neoplasms. Cell 66, 649–61.

Estreicher, A., and Iggo, R. (1996). Retrovirus-mediated p53 gene therapy. Nature Med 2, 1163.

Fisher, A. L., and Caudy, M. (1998). Groucho proteins: transcriptional corepressors for specific subsets of DNA-binding transcription factors in vertebrates and invertebrates. Genes Dev 12, 1931–40.

Flaman, J. M., Frebourg, T., Moreau, V., Charbonnier, F., Martin, C., Ishioka, C., Friend, S. H., and Iggo, R. (1994). A rapid PCR fidelity assay. Nucleic Acids Res 22, 3259–60.

Gagnebin, J., Kovar, H., Kajava, A. V., Estreicher, A., Jug, G., Monnier, P., and Iggo, R. (1998). Use of transcription reporters with novel p53 binding sites to target tumour cells expressing endogenous or virally transduced p53 mutants with altered sequence-specificity. Oncogene 16, 685–90.

He, T. C., Zhou, S., da Costa, L. T., Yu, J., Kinzler, K. W., and Vogelstein, B. (1998). A simplified system for generating recombinant adenoviruses. Proc Natl Acad Sci U S A 95, 2509–14.

Heise, C., Sampson-Johannes, A., Williams, A., McCormick, F., Von Hoff, D. D., and Kim, D. H. (1997). ONYX-015, an E1B gene-attenuated adenovirus, causes tumor-specific cytolysis and antitumoral efficacy that can be augmented by standard chemotherapeutic agents. Nature Med 3, 639–645.

Huang, M. M., and Hearing, P. (1989). The adenovirus early region 4 open reading frame 6/7 protein regulates the DNA binding activity of the cellular transcription factor, E2F, through a direct complex. Genes Dev 3, 1699–710.

Hurst, H. C., and Jones, N. C. (1987). Identification of factors that interact with the E1A-inducible adenovirus E3 promoter. Genes Dev 1, 1132–46.

Jarriault, S., Brou, C., Logeat, F., Schroeter, E. H., Kopan, R., and Israel, A. (1995). Signalling downstream of activated mammalian Notch. Nature 377, 355–8.

Kemeny, N., Daly, J., Reichman, B., Geller, N., Botet, J., and Oderman, P. (1987). Intrahepatic or systemic infusion of fluorodeoxyuridine in patients with liver metastases from colorectal carcinoma. A randomized trial. Ann Intern Med 107, 459–65.

Kemeny, N., Seiter, K., Niedzwiecki, D., Chapman, D., Sigurdson, E., Cohen, A., Botet, J., Oderman, P., and Murray, P. (1992). A randomized trial of intrahepatic infusion of fluorodeoxyuridine with dexamethasone versus fluorodeoxyuridine alone in the treatment of metastatic colorectal cancer. Cancer 69, 327–34.

Ketner, G., Spencer, F., Tugendreich, S., Connelly, C., and Hieter, P. (1994). Efficient manipulation of the human adenovirus genome as an infectious yeast artificial chromosome clone. Proc Natl Acad Sci U S A 91, 6186–90.

Korinek, V., Barker, N., Morin, P. J., van Wichen, D., de Weger, R., Kinzler, K. W., Vogelstein, B., and Clevers, H. (1997). Constitutive transcriptional activation by a beta-catenin-Tcf complex in APC-/- colon carcinoma. Science 275, 1784–7.

Labianca, R., Pessi, M. A., and Zamparelli, G. (1997). Treatment of colorectal cancer. Current guidelines and future prospects for drug therapy. Drugs 53, 593–607.

Leyvraz, S., Spataro, V., Bauer, J., Pampallona, S., Salmon, R., Dorval, T., Meuli, R., Gillet, M., Lejeune, F., and Zografos, L. (1997). Treatment of ocular melanoma metastatic to the liver by hepatic arterial chemotherapy. J Clin Oncol 15, 2589–95.

Morin, P. J., Sparks, A. B., Korinek, V., Barker, N., Clevers, H., Vogelstein, B., and Kinzler, K. W. (1997). Activation of beta-catenin-Tcf signaling in colon cancer by mutations in beta-catenin or APC. Science 275, 1787–90.

Ogawa, N., Fujiwara, T., Kagawa, S., Nishizaki, M., Morimoto, Y., Tanida, T., Hizuta, A., Yasuda, T., Roth, J. A., and Tanaka, N. (1997). Novel combination therapy for human colon cancer with adenovirus- mediated wild-type p53 gene transfer and DNA-damaging chemotherapeutic agent. Int J Cancer 73, 367–70.

Parr, M. J., Manome, Y., Tanaka, T., Wen, P., Kufe, D. W., Kaelin, W. G., and Fine, H. A. (1997). Tumor-Selective Transgene Expression In Vivo Mediated By an E2f-Responsive Adenoviral Vector. Nature Medicine 3, 1145–1149.

Patt, Y. Z., and Mavligit, G. M. (1991). Arterial chemotherapy in the management of colorectal cancer: an overview. Semin Oncol 18, 478–90.

Qian, C., Bilbao, R., Bruna, O., and Prieto, J. (1995). Induction of sensitivity to ganciclovir in human hepatocellular carcinoma cells by adenovirus-mediated gene transfer of herpes simplex virus thymidine kinase. Hepatology 22, 118–23.

Roth, J. A., and Cristiano, R. J. (1997). Gene therapy for cancer: what have we done and where are we going? J Natl Cancer Inst 89, 21–39.

Roth, J. A., Nguyen, D., Lawrence, D. D., Kemp, B. L., Carrasco, C. H., Ferson, D. Z., Hong, W. K., Komaki, R., Lee, J. J., Nesbitt, J. C., Pisters, K. M., Putnam, J. B., Schea, R., Shin, D. M., Walsh, G. L., Dolormente, M. M., Han, C. I., Martin, F. D., Yen, N., Xu, K., Stephens, L. C., McDonnell, T. J., Mukhopadhyay, T., and Cai, D. (1996). Retrovirus-mediated wild-type p53 gene transfer to tumors of patients with lung cancer. Nature Med 2, 985–991.

Rubinfeld, B., Robbins, P., El-Gamil, M., Albert, I., Porfiri, E., and Polakis, P. (1997). Stabilization of beta-catenin by genetic defects in melanoma cell lines. Science 275, 1790–2.

Sandig, V., Brand, K., Herwig, S., Lukas, J., Bartek, J., and Strauss, M. (1997). Adenovirally transferred p16INK4/CDKN2 and p53 genes cooperate to induce apoptotic tumor cell death. Nat Med 3, 313–9.

Shenk, T. (1996). Adenoviridae: the viruses and their replication. In Fields Virology, D. M. K. B. N. Fields, P. M. Howley et al., ed. (Philadelphia: Lippincott-Raven Publishers), pp. 2111–2148.

Stevenson, S. C., Rollence, M., Marshall-Neff, J., and McClelland, A. (1997). Selective targeting of human cells by a chimeric adenovirus vector containing a modified fiber protein. J Virol 71, 4782–90.

Stone, D. M., Hynes, M., Armanini, M., Swanson, T. A., Gu, Q., Johnson, R. L., Scott, M. P., Pennica, D., Goddard, A., Phillips, H., Noll, M., Hooper, J. E., de Sauvage, F., and Rosenthal, A. (1996). The tumour-suppressor gene patched encodes a candidate receptor for Sonic hedgehog. Nature 384, 129–34.

Stupp, R., Focan, C., Sessa, C., Nowacki, M., Vindevoghel, A., Canon, J. L., Zaluski, J., Oulid-Aissa, D., Boussard, B., and Pestalozzi, B. (1998). Prophylactic use of antibiotics during treatment with CPT-11 for metastatic colorectal cancer. A randomized multicenter trial. Ann Oncol in press.

Van de Wetering, M., Cavallo, R., Dooijes, D., van Beest, M., van Es, J., Loureiro, J., Ypma, A., Hursh, D., Jones, T., Bejsovec, A., Peifer, M., Mortin, M., and Clevers, H. (1997). Armadillo coactivates transcription driven by the product of the Drosophila segment polarity gene dTCF. Cell 88, 789–99.

Van der Eb, M. M., Cramer, S. J., Vergouwe, Y., Schagen, F. H., van Krieken, J. H., van der Eb, A. J., Rinkes, I. H., van de Velde, C. J., and Hoeben, R. C. (1998). Severe hepatic dysfunction after adenovirus-mediated transfer of the herpes simplex virus thymidine kinase gene and ganciclovir administration. Gene Ther 5, 451–8.

Xie, J., Murone, M., Luoh, S. M., Ryan, A., Gu, Q., Zhang, C., Bonifas, J. M., Lam, C. W., Hynes, M., Goddard, A., Rosenthal, A., Epstein, E. H., Jr., and de Sauvage, F. J. (1998). Activating Smoothened mutations in sporadic basal-cell carcinoma. Nature 391, 90–2.

What is claimed is:

1. A viral DNA construct encoding for an adenovirus capable of replication in a human or animal tumour cell and causing death of such tumour cells comprising one or more selected transcription factor binding sites for a transcription factor the level or activity of which is increased in a human or animal tumour cell relative to that of a normal human or animal cell of the same type operatively positioned together with early viral protein gene open reading frames such as to promote expression of these open reading frames in the presence of said selected transcription factor, the protein products of those open reading frames being mechanistically directly involved in viral construct nucleic acid replication selected from the group consisting of viral polymerase, primase, nuclease, helicase, ligase, DNA terminal protein and DNA binding protein and wherein the construct encodes an adenovirus E3 promoter which has in one or more mutations to nucleotide residues which modify or delete transcription factor binding sites, as related to wild type adenovirus, selected from those in the NF1, NFKB, AP1 and ATF regions.

2. A viral DNA construct as claimed in claim 1 having a nucleic acid sequence corresponding to that of a wild type virus sequence wherein it has one or more wild type transcription factor binding sites replaced by one or more selected transcription factor binding sites, these selected sites being operatively positioned in one or more promoter regions which control expression of early genes such as to promote expression in the presence of said selected transcription factor, the protein products of those genes being mechanistically directly involved in viral nucleic acid replication and wherein the selected transcription, factor binding sites are for a transcription factor the level or activity of which is increased in a human or animal tumour cell relative to that of a normal human or animal cell of the same type.

3. A viral DNA construct as claimed in claim 1 wherein the selected transcription factor binding sites are for a transcription factor whose activity or level is specifically increased by causal oncogenic mutations.

4. A construct as claimed in claim 1 wherein its nucleic acid sequence, other than the selected sites, corresponds to that of the genome of adenovirus Ad5, Ad40 or Ad41, or its nucleic acid sequence incorporates DNA encoding for fibre protein from Ad5, Ad40 or Ad41, optionally with 15 to 25 lysines added to the end thereof.

5. A construct as claimed in claim 1 wherein the genes controlled by the selected transcription factor binding site are DNA polymerase, DNA terminal protein and/or DNA binding protein.

6. A construct as claimed in claim 1 wherein its nucleic acid sequence corresponds to that of an adenovirus having a wild type E2 early promoter transcription factor binding site replaced by the tumour cell specific transcription factor binding site.

7. A construct as claimed in claim 1 wherein it encodes a functional viral RNA export capacity.

8. A construct as claimed in claim 1 having a nucleic acid sequence corresponding to that of an adenovirus wherein, in the E1 region, the E1B 55K gene is functional and/or intact.

9. A construct as claimed in claim 2 wherein the selected transcription factor binding site used in place of wild type site is selected from Tcf-4, RBPJK, Gli-I, HIF1alpha and telomerase promoter binding sites.

10. A construct as claimed in claim 2 wherein the transcription factor binding site that replaces the wild type site is selectively activated in tumour cells containing oncogenic APC and β-catenin mutations.

11. A construct as claimed in claim 2 wherein the transcription factor binding site that replaces the wild type site is a single or multiple Tcf-4 binding site sequence.

12. A construct as claimed in claim 11 wherein it comprises from 2 to 20 Tcf-4 binding site sequences at each replaced promoter site.

13. A construct as claimed in claim 1 wherein the mutations reduce E2 gene transcription caused by E3 promoter activity.

14. A construct as claimed in claim 1 wherein the mutations are silent mutations, being such as not to alter the predicted protein sequence of any viral protein, but which alter the activity of one or more viral promoters.

15. A construct as claimed in claim 1 wherein its sequence corresponds to that of an adenovirus genome wherein a region in the E2 early promoter, which is not overlapped by coding sequence, is replaced with multiple Tcf-4 binding site sequences.

16. A construct as claimed in claim 1 wherein its sequence corresponds to that of an adenovirus genome wherein the E2 late promoter en inactivated with silent mutations.

17. A virus comprising or encoded by a DNA construct as claimed in claim 1.

18. A method of manufacture of a viral DNA construct as claimed in claim 2 comprising transforming a viral genome having one or more wild type transcription factor binding sites controlling transcription of genes having protein products directly mechanistically involved in viral nucleic acid replication to replace one or more of these by tumour specific transcription factor binding sites.

19. A method as claimed in claim 18 wherein the viral genome is cloned by gap repair in a circular YAC/BAC in yeast.

20. A method as claimed in claim 18 wherein the genome is modified by two step gene replacement.

21. A method as claimed in claim 18 wherein the modified genome is transferred to a prokaryote for production of viral construct DNA.

22. A method of manufacture of a virus comprising transferring viral construct DNA produced by a method as claimed in claim 18 to a mammalian cell for production of virus.

23. A method for treating a patient suffering from neoplasms comprising causing a viral DNA construct or virus as claimed in claim 1 to infect tissues of the patient, including or restricted to those of the neoplasm, and allowing replication such that neoplasm cells are caused to be killed.

* * * * *

SEQUENCE LISTING

```
<160> NUMBER OF SEQ ID NOS: 45

<210> SEQ ID NO 1
<211> LENGTH: 752
<212> TYPE: DNA
<213> ORGANISM: ADENOVIRUS VR5
<220> FEATURE:
<221> NAME/KEY: promoter
<222> LOCATION: (250)..(302)

<400> SEQUENCE: 1
ggagcgctgc gtctggcgcc caacgaaccc gtatcgaccc gcgagcttag aaacaggatt      60
tttcccactc tgtatgctat atttaacag agcaggggcc aagaacaaga gctgaaaata     120
aaaaacaggt ctctgcgatc cctcacccgc agctgcctgt atcacaaaag cgaagatcag     180
cttcggcgca cgctggaaga cgcggaggct ctcttcagta aatactgcgc gctgactctt     240
aaggactaga tcaaagggtt ggagatcaaa gggatccaga tcaaagggat taagatcaaa     300
gggccattat gagcaaggaa attcccacgc cctacatgtg gagttaccag ccacaaatgg     360
gacttgcggc tggagctgcc caagactact caacccgaat aaactacatg agcgcgggac     420
cccacatgat atcccgggtc aacggaatcc gcgcccaccg aaaccgaatt ctcttggaac     480
aggcggctat taccaccaca cctcgtaata accttaatcc ccgtagttgg cccgctgcac     540
tggtgtacca agagagccca gctcccacca ctgtagtgct gccaagagac gcccaggccg     600
aagttcagat gaccaatagc ggggcgcagc ttgcgggcgg ctttagacac agggtgcggt     660
cgcccgggca gggtataact cacctgacaa tcagagggcg aggtattcag ctcaacgacg     720
agtcggtgag ctcctcgctt ggtctccgtc cg                                   752

<210> SEQ ID NO 2
<211> LENGTH: 82
<212> TYPE: PRT
```

```
<213> ORGANISM: ADENOVIRUS VR5

<400> SEQUENCE: 2

Gly Ala Leu Arg Leu Ala Pro Asn Glu Pro Val Ser Thr Arg Glu Leu
 1               5                  10                  15

Arg Asn Arg Ile Phe Pro Thr Leu Tyr Ala Ile Phe Gln Gln Ser Arg
                20                  25                  30

Gly Gln Glu Gln Glu Leu Lys Ile Lys Asn Arg Ser Leu Arg Ser Leu
            35                  40                  45

Thr Arg Ser Cys Leu Tyr His Lys Ser Glu Asp Gln Leu Arg Arg Thr
    50                  55                  60

Leu Glu Asp Ala Glu Ala Leu Phe Ser Lys Tyr Cys Ala Leu Thr Leu
65                  70                  75                  80

Lys Asp

<210> SEQ ID NO 3
<211> LENGTH: 148
<212> TYPE: PRT
<213> ORGANISM: ADENOVIRUS VR5

<400> SEQUENCE: 3

Met Ser Lys Glu Ile Pro Thr Pro Tyr Met Trp Ser Tyr Gln Pro Gln
 1               5                  10                  15

Met Gly Leu Ala Ala Gly Ala Ala Gln Asp Tyr Ser Thr Arg Ile Asn
                20                  25                  30

Tyr Met Ser Ala Gly Pro His Met Ile Ser Arg Val Asn Gly Ile Arg
            35                  40                  45

Ala His Arg Asn Arg Ile Leu Leu Glu Gln Ala Ala Ile Thr Thr Thr
    50                  55                  60

Pro Arg Asn Asn Leu Asn Pro Arg Ser Trp Pro Ala Ala Leu Val Tyr
65                  70                  75                  80

Gln Glu Ser Pro Ala Pro Thr Thr Val Val Leu Pro Arg Asp Ala Gln
                85                  90                  95

Ala Glu Val Gln Met Thr Asn Ser Gly Ala Gln Leu Ala Gly Gly Phe
            100                 105                 110

Arg His Arg Val Arg Ser Pro Gly Gln Gly Ile Thr His Leu Thr Ile
        115                 120                 125

Arg Gly Arg Gly Ile Gln Leu Asn Asp Glu Ser Val Ser Ser Ser Leu
    130                 135                 140

Gly Leu Arg Pro
145

<210> SEQ ID NO 4
<211> LENGTH: 780
<212> TYPE: DNA
<213> ORGANISM: ADENOVIRUS VR5

<400> SEQUENCE: 4
ggagcgctgc gtctggcgcc caacgaaccc gtatcgaccc gcgagcttag aaacaggatt        60
tttcccactc tgtatgctat atttcaacag agcaggggcc aagaacaaga gctgaaaata      120
aaaaacaggt ctctgcgatc cctcacccgc agctgcctgt atcacaaaag cgaagatcag      180
cttcggcgca cgctggaaga cgcggaggct ctcttcagta aatactgcgc gctgactctt      240
aaggactagt ttcgcgccct ttctcaaatt taagcgcgaa aactacgtca tctccagcgg      300
ccacacccgg cgccagcacc tgtcgtcagc gccattatga gcaaggaaat tcccacgccc      360
```

```
tacatgtgga gttaccagcc acaaatggga cttgcggctg gagctgccca agactactca      420
acccgaataa actacatgag cgcgggaccc cacatgatat cccgggtcaa cggaatccgc      480
gcccaccgaa accgaattct cttggaacag gcggctatta ccaccacacc tcgtaataac      540
cttaatcccc gtagttggcc cgctgccctg gtgtaccagg aaagtcccgc tcccaccact      600
gtggtacttc ccagagacgc ccaggccgaa gttcagatga ctaactcagg ggcgcagctt      660
gcgggcggct ttcgtcacag ggtgcggtcg cccgggcagg gtataactca cctgacaatc      720
agagggcgag gtattcagct caacgacgag tcggtgagct cctcgcttgg tctccgtccg      780
```

<210> SEQ ID NO 5
<211> LENGTH: 209
<212> TYPE: DNA
<213> ORGANISM: ADENOVIRUS VR5

<400> SEQUENCE: 5

```
tcgcctgacg aaaagtccgc ggctccgggg ttgaaactca ctccggggct gtggacgtcg       60
gcttaccttc gcaaatttgt acctgaggac taccacgccc acgagattag gttctacgaa      120
gatcagtccc gcccgccaaa tgcggagctt accgcctgcg tcattaccca gggccacatt      180
cttggccaat tgcaagccat caacaaagc                                        209
```

<210> SEQ ID NO 6
<211> LENGTH: 69
<212> TYPE: PRT
<213> ORGANISM: ADENOVIRUS VR5

<400> SEQUENCE: 6

```
Ser Pro Asp Glu Lys Ser Ala Ala Pro Gly Leu Lys Leu Thr Pro Gly
  1               5                  10                  15

Leu Trp Thr Ser Ala Tyr Leu Arg Lys Phe Val Pro Glu Asp Tyr His
             20                  25                  30

Ala His Glu Ile Arg Phe Tyr Glu Asp Gln Ser Arg Pro Pro Asn Ala
         35                  40                  45

Glu Leu Thr Ala Cys Val Ile Thr Gln Gly His Ile Leu Gly Gln Leu
     50                  55                  60

Gln Ala Ile Asn Lys
 65
```

<210> SEQ ID NO 7
<211> LENGTH: 180
<212> TYPE: DNA
<213> ORGANISM: ADENOVIRUS VR5

<400> SEQUENCE: 7

```
atgtaagttt aataaagggt gagataatgt ttaacttgca tggcgtgtta aatccctttg       60
atcttaatcc ctttgatctg gatcccttg atctccaacc ctttgatcta gtcctatata      120
atgcgccgtg ggctaatctt ggttacatct gacctcatgg aggcttggga gtgtttggaa      180
```

<210> SEQ ID NO 8
<211> LENGTH: 314
<212> TYPE: DNA
<213> ORGANISM: Homo sapiens

<400> SEQUENCE: 8

```
agcagctgcg ctgtcggggc caggccgggc tcccagtgga ttcgcgggca cagacgccca       60
ggaccgcgct ccccacgtgg cggagggact ggggacccgg gcaccgtcc tgccccttca      120
```

-continued

| | |
|---|---|
| ccttccagct ccgcctcctc cgcgcggacc ccgccccgtc ccgacccctc ccgggtcccc | 180 |
| ggcccagccc cctccgggcc tcccagcccc cccctttcct ttccgcggcc ccgccctctc | 240 |
| ctcgcggcgc gagtttcagg cagcgctgcg tcctgctgcg cacgtgggaa gccctggccc | 300 |
| cggccacccc cgcg | 314 |

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 9

| | |
|---|---|
| tgcattggta ccgtcatctc ta | 22 |

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 10

| | |
|---|---|
| gttgctctgc ctctccactt | 20 |

<210> SEQ ID NO 11
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 11

| | |
|---|---|
| cagatcaaag ggattaagat caaagggcca ttatgagcaa g | 41 |

<210> SEQ ID NO 12
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 12

| | |
|---|---|
| gatccctttg atctccaacc ctttgatcta gtccttaaga gtc | 43 |

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 13

| | |
|---|---|
| gggcgagtct ccacgtaaac g | 21 |

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 14

| | |
|---|---|
| gggcaccagc tcaatcagtc a | 21 |

<210> SEQ ID NO 15
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 15
cggaattcaa gcttaattaa catcatcaat aatatacc                            38

<210> SEQ ID NO 16
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 16
gcggctagcc accatggagc gaagaaaccc a                                   31

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 17
gccaccggta caacattcat t                                              21

<210> SEQ ID NO 18
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 18
agctgggctc tcttggtaca ccagtgcagc gggccaacta                          40

<210> SEQ ID NO 19
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 19
cccaccactg tagtgctgcc aagagacgcc caggccgaag tt                       42

<210> SEQ ID NO 20
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 20
ctgcgccccg ctattggtca tctgaacttc ggcctg                              36

<210> SEQ ID NO 21
<211> LENGTH: 32
<212> TYPE: DNA
<213> ORGANISM: Artificial Sequence
<220> FEATURE:

<223> OTHER INFORMATION: Description of Artificial Sequence: Primer

<400> SEQUENCE: 21
cttgcgggcg gctttagaca cagggtgcgg tc 32

<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 22
cagatcaaag ggccattatg agcaag 26

<210> SEQ ID NO 23
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 23 gatcccttg atctagtcct taagagtc 28

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 24
atggcacaaa ctcctcaata a 21

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 25
ccaagactac tcaacccgaa ta 22

<210> SEQ ID NO 26
<211> LENGTH: 11
<212> TYPE: DNA
<213> ORGANISM: Homo sapiens

<400> SEQUENCE: 26
agatcaaagg g 11

<210> SEQ ID NO 27
<211> LENGTH: 35
<212> TYPE: DNA
<213> ORGANISM: Homo sapiens

<400> SEQUENCE: 27
gactagatca aagggatcca gatcaaaggg ccatt 35

<210> SEQ ID NO 28
<211> LENGTH: 64
<212> TYPE: DNA
<213> ORGANISM: Homo sapiens

<400> SEQUENCE: 28
gactagatca agggttggag atcaaaggga tccagatcaa agggattaag atcaaagggc    60
catt                                                                 64

<210> SEQ ID NO 29
<211> LENGTH: 65
<212> TYPE: DNA
<213> ORGANISM: Homo sapiens

<400> SEQUENCE: 29
gactagatca aagggttgga gatcaaaggg atccagatca aagggattaa gatcaaaggg    60
ccatt                                                                65

<210> SEQ ID NO 30
<211> LENGTH: 48
<212> TYPE: DNA
<213> ORGANISM: Artificial Sequence
<220> FEATURE:
<223> OTHER INFORMATION: Description of Artificial Sequence: Primer

<400> SEQUENCE: 30 tcccttttgat ctccaaccct ttgatctagt cctatataat gcgccgtg               48

<210> SEQ ID NO 31
<211> LENGTH: 47
<212> TYPE: DNA
<213> ORGANISM: Artificial Sequence
<220> FEATURE:
<223> OTHER INFORMATION: Description of Artificial Sequence: Primer

<400> SEQUENCE: 31
tccagatcaa agggattaag atcaaaggga tttaacacgc catgcaa                 47

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Taqman
      oligo

<400> SEQUENCE: 32
ttcgcttttg tgatacaggc a                                             21

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Taqman
      oligo

<400> SEQUENCE: 33
gtcttggacg cgacgagaag                                               20

<210> SEQ ID NO 34
<211> LENGTH: 17
<212> TYPE: DNA
<213> ORGANISM: Artificial Sequence
<220> FEATURE:
<223> OTHER INFORMATION: Description of Artificial Sequence: Taqman
      oligo

<400> SEQUENCE: 34
cggagcgttt gccgcgc                                                      17

<210> SEQ ID NO 35
<211> LENGTH: 17
<212> TYPE: DNA
<213> ORGANISM: Artificial Sequence
<220> FEATURE:
<223> OTHER INFORMATION: Description of Artificial Sequence: Taqman
      oligo

<400> SEQUENCE: 35
cggagcgttt gccgcgc                                                      17

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Taqman
      oligo

<400> SEQUENCE: 36
aacacctggt ccactgtcgc                                                   20

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Taqman
      oligo

<400> SEQUENCE: 37
ccgcgactcc gtttcaaccc aga                                               23

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Taqman
      oligo

<400> SEQUENCE: 38
tgcttccatc aaacgagttg g                                                 21

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Taqman
      oligo

<400> SEQUENCE: 39
gcgctgagtt tggctctagc                                                   20

<210> SEQ ID NO 40
<211> LENGTH: 26
<212> TYPE: DNA
<213> ORGANISM: Artificial Sequence
<220> FEATURE:
<223> OTHER INFORMATION: Description of Artificial Sequence: Taqman
      oligo

<400> SEQUENCE: 40

-continued

```
cggcggctgc tcaatctgta tcttca                                26
```

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Taqman
      oligo

<400> SEQUENCE: 41

```
ggttgattca tcggtcagtg c                                     21
```

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Taqman
      oligo

<400> SEQUENCE: 42

```
acgcctgcgg gtatgtattc                                       20
```

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Taqman
      oligo

<400> SEQUENCE: 43

```
aaaagcgacc gaaatagccc g                                     21
```

<210> SEQ ID NO 44
<211> LENGTH: 23
<212> TYPE: DNA
<213> ORGANISM: Artificial Sequence
<220> FEATURE:
<223> OTHER INFORMATION: Description of Artificial Sequence: Taqman
      oligo

<400> SEQUENCE: 44

```
tgatgtttga cgctacagcc ata                                   23
```

<210> SEQ ID NO 45
<211> LENGTH: 23
<212> TYPE: DNA
<213> ORGANISM: Artificial Sequence
<220> FEATURE:
<223> OTHER INFORMATION: Description of Artificial Sequence: Taqman
      oligo

<400> SEQUENCE: 45

```
gggatttgtg tttggtgcat tag                                   23
```